(12) United States Patent
Debacq et al.

(10) Patent No.: US 12,214,087 B2
(45) Date of Patent: Feb. 4, 2025

(54) THERMOSTABLE QUICK-DISSOLVING THIN FILM

(71) Applicants: GLAXOSMITHKLINE BIOLOGICALS SA, Rixensart (BE); ARIDIS PHARMACEUTICALS, INC., San Jose, CA (US)

(72) Inventors: Christophe Debacq, Rixensart (BE); Phillip Lovalenti, San Jose, CA (US); Van Nguyen, San Jose, CA (US); Laurence Plapied, Rixensart (BE); Laurent Strodiot, Rixensart (BE); Austin Wuerfel, San Jose, CA (US)

( * ) Notice: Subject to any disclaimer, the term of this patent is extended or adjusted under 35 U.S.C. 154(b) by 587 days.

(21) Appl. No.: 17/438,116

(22) PCT Filed: Mar. 17, 2020

(86) PCT No.: PCT/EP2020/057268
§ 371 (c)(1),
(2) Date: Sep. 10, 2021

(87) PCT Pub. No.: WO2020/187903
PCT Pub. Date: Sep. 24, 2020

(65) Prior Publication Data
US 2022/0183993 A1   Jun. 16, 2022

Related U.S. Application Data

(60) Provisional application No. 62/820,432, filed on Mar. 19, 2019.

(51) Int. Cl.
| | | |
|---|---|---|
| *A61K 9/70* | (2006.01) | |
| *A61K 9/00* | (2006.01) | |
| *A61K 47/12* | (2006.01) | |
| *A61K 47/18* | (2017.01) | |
| *A61K 47/22* | (2006.01) | |
| *A61K 47/26* | (2006.01) | |
| *A61K 47/32* | (2006.01) | |

(52) U.S. Cl.
CPC ............ *A61K 9/7007* (2013.01); *A61K 9/006* (2013.01); *A61K 47/12* (2013.01); *A61K 47/183* (2013.01); *A61K 47/22* (2013.01); *A61K 47/26* (2013.01); *A61K 47/32* (2013.01)

(58) Field of Classification Search
None
See application file for complete search history.

(56) References Cited

FOREIGN PATENT DOCUMENTS

| WO | 2010/002418 A2 | 1/2010 |
|---|---|---|
| WO | 2012/103464 A2 | 8/2012 |
| WO | 2017/214187 A1 | 12/2017 |
| WO | 2018/041891 A1 | 3/2018 |
| WO | 2018/053524 A1 | 3/2018 |

*Primary Examiner* — Robert A Wax
*Assistant Examiner* — Quanglong N Truong
(74) *Attorney, Agent, or Firm* — Romit Majumdar

(57) ABSTRACT

The present invention relates to thermostable quick-dissolving thin films comprising a biological moiety and an excipient mix which are suitable for the formulation of biological moieties such as viral vaccines, to methods for manufacturing such thermostable quick-dissolving thin films, and to their use in therapy. The excipient mix comprises one or more water-soluble polymer(s), a sugar selected from sucrose, trehalose and a combination thereof, a metal ion, a carboxylate, and a buffering agent.

20 Claims, 18 Drawing Sheets

THERMOSTABLE QUICK-DISSOLVING THIN FILM

CROSS-REFERENCE TO RELATED APPLICATIONS

This application is filed pursuant to 35 U.S.C. § 371 as a United States National Phase Application of International Application No. PCT/EP2020/057268 filed 17 Mar. 2020 which claims priority from U.S. Provisional No. 62/820,432 filed 19 Mar. 2019.

The present invention relates to thermostable quick-dissolving thin films which are suitable for the formulation of biological moieties such as viral vaccines.

BACKGROUND OF THE INVENTION

The temperature sensitivity of biologicals such as vaccines is a challenge in terms of formulation and means they usually need to be stored and transported at refrigeration temperatures (2° C. to 8° C.) and administered immediately after removal from refrigeration. This necessitates strict cold chain storage and transport which is problematic particularly in developing and low-income regions where the cold chain as required is imperfect, overburdened or non-existent. Improving vaccine formulation thermostability could have a major impact on public health in such regions by allowing to (i) increase vaccine coverage by enabling the stocking of vaccines at facilities that do not have cold chain equipment and by facilitating outreach; (ii) improve efficacy by decreasing the probability of administering vaccines whose efficacy was impaired by heat and/or freeze exposure and (iii) reduce total system costs by decreasing vaccine wastage due to detected heat and freeze exposures, by decreasing the cold chain footprint, and by reducing the overall requirements for the vaccine delivery supply chain (Karp et al., Vaccine 2015 33(30):3471-3479).

Rotaviruses have been recognised as one of the most important causes of severe diarrhoea in infants and young children (Estes, M. K. Rotaviruses and Their Replication in Fields Virology, Third Edition, edited by Fields et al., Raven Publishers, Philadelphia, 1996). It is estimated that rotavirus disease is responsible for over 600,000 deaths annually. Rotavirus-induced illness most commonly affects children between 6 and 24 months of age, and the peak prevalence of the disease generally occurs during the cooler months in temperate climates, and year-round in tropical areas. Rotaviruses are typically transmitted from person to person by the faecal-oral route with an incubation period of from about 1 to about 3 days. Unlike infection in the 6-month to 24-month age group, neonates are generally asymptomatic or have only mild disease. In contrast to the severe disease normally encountered in young children, most adults are protected as a result of previous rotavirus infection so most adult infections are mild or asymptomatic (Offit, P. A. et al. Comp. Ther., 8(8):21-26, 1982).

Examples of commercially available rotavirus vaccines include ROTARIX and ROTATEQ. ROTARIX is a live attenuated monovalent vaccine derived from the human 89-12 strain which belongs to the G1P[8] type, indicated for the prevention of rotavirus gastroenteritis caused by G1 and non-G1 types (G3, G4, and G9) when administered orally as a 2-dose series in infants. ROTARIX is available in a lyophilised form and in a liquid form both of which need to be stored at 2° to 8° C. ROTATEQ is a live pentavalent human-bovine reassortant vaccine, in a liquid form, administered orally as a 3-dose series in infants. ROTATEQ also needs to be stored at 2° to 8° C.

Oral thin films (OTFs) are used for oral administration of small molecules and offer the advantage of significantly reducing storage space, of allowing easy administration and of guaranteeing the entire dose is delivered. In particular, young children and infants may spit out part of a drug administered in a liquid form in which case the full dose is not administered. The use of an OTF circumvents that risk. Oral thin films typically contain water-soluble polymers which have good mucoadhesive properties and cause the thin film to strongly adhere to mucosal tissue until complete dissolution. Examples include breath fresheners such as Listerine and small molecule prescription medications such as Suboxone, Zuplenz, ONSOLIS or BUNAVAIL. Oral thin films are however not commonly used for more complex biological products such as vaccines.

WO2017214187 discloses methods for preparing quick dissolving thin films containing a bioactive material, and that preferred formulations for an oral thin film containing a virus and in particular a rotavirus, contain potassium phosphate, citrate, sucrose, sorbitol, calcium ions, zinc ions, and gelatin, in combination with a PVA matrix polymer.

Gelatin, which is used in the pharmaceutical industry as a stabilizer, is a by-product from the meat industry and carries the risk of transmitting animal diseases, for example bovine spongiform encephalopathy (BSE).

It is an objective of the present invention to provide thermostable quick-dissolving thin films for biologicals and more particularly viral vaccines, which do not need to be refrigerated for storage and which are free of animal derived stabilizers such as gelatin or albumin.

SUMMARY OF THE INVENTION

In a first aspect, the present invention provides a quick-dissolving thin film comprising a biological moiety and an excipient mix, wherein said excipient mix comprises
  one or more water-soluble polymer(s),
  a sugar selected from sucrose, trehalose and a combination thereof,
  a metal ion,
  a carboxylate, and
  a buffering agent,
wherein said quick-dissolving thin film is thermostable.

In another aspect, the present invention provides a quick-dissolving thin film consisting of a biological moiety, an excipient mix, and optionally an antacid, wherein said excipient mix consists of
  one or more water-soluble polymer(s),
  a sugar selected from sucrose, trehalose and a combination thereof,
  a metal ion,
  a carboxylate,
  a buffering agent, and
  optionally one or more amino acids,
wherein said quick-dissolving thin film is thermostable.

In one aspect, the present invention provides a quick-dissolving thin film of the invention for use in therapy.

In a further aspect, the present invention provides a quick-dissolving thin film of the invention for use in the prevention or treatment of an infectious disease in a subject.

In a further aspect, the invention provides the use of a quick-dissolving thin film of the invention in the manufacture of a medicament for use in the treatment or prevention of an infectious disease in a subject.

In a further aspect, the invention provides a method for the treatment or prevention of an infectious disease in a subject comprising administering a quick-dissolving thin film of the invention to a subject.

In a further aspect, the present invention provides a kit comprising the quick-dissolving thin film of the invention in a sterile packaging and instructions for use of the kit.

In a further aspect, the present invention provides a method for preparing a thermostable quick-dissolving thin film comprising:
a) preparing an aqueous solution comprising or consisting of
  a biological moiety,
  one or more water-soluble polymer(s),
  a sugar selected from sucrose, trehalose and a combination thereof,
  a meal ion,
  a carboxylate, and
  one or more buffering agents,
b) adjusting the pH of the aqueous solution to a value comprised between 5 and 9,
c) applying the aqueous solution on a drying surface,
d) drying the aqueous solution to obtain a thin film, and
e) removing the dried thin film from the drying surface, thereby obtaining said thermostable quick-dissolving thin film.

In a further aspect, the invention provides a thermostable quick-dissolving thin film obtainable by the method of the invention.

DETAILED DESCRIPTION OF THE INVENTION

Figure 1:
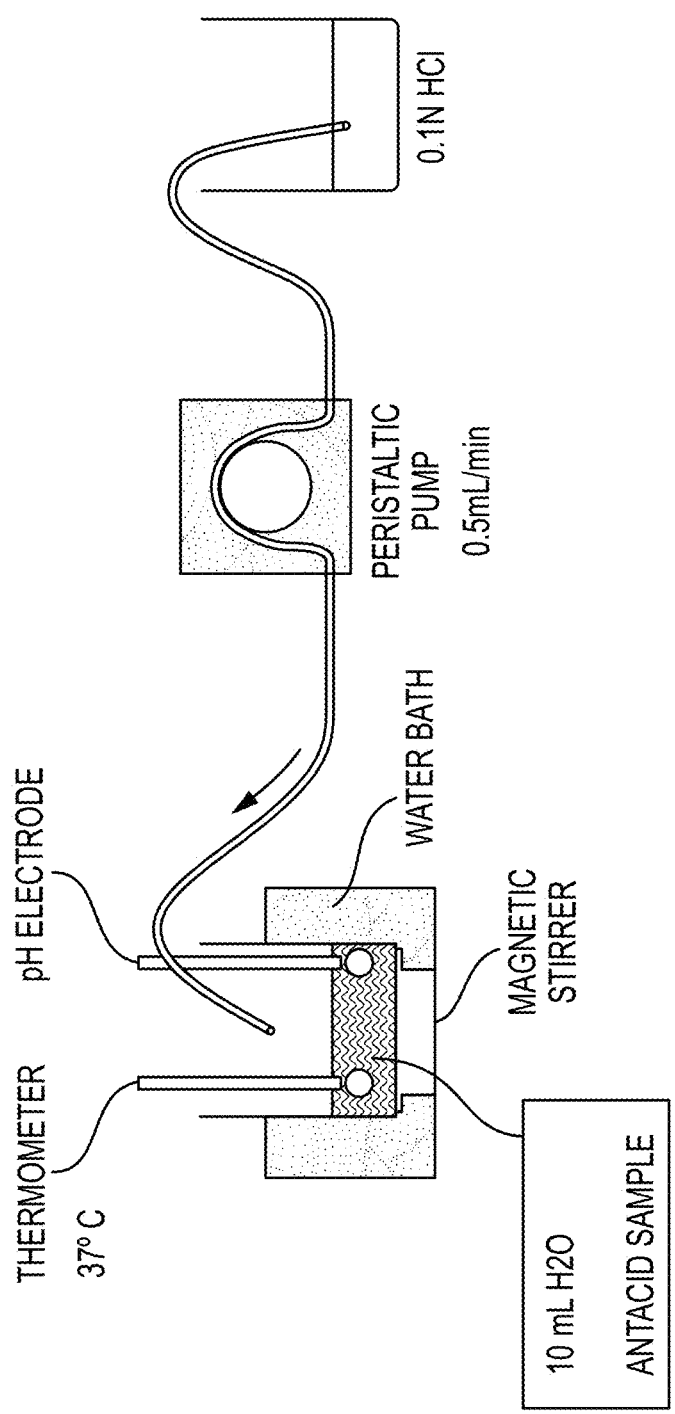
FIG. 1—Baby Rossett-Rice testing
Figure 2:
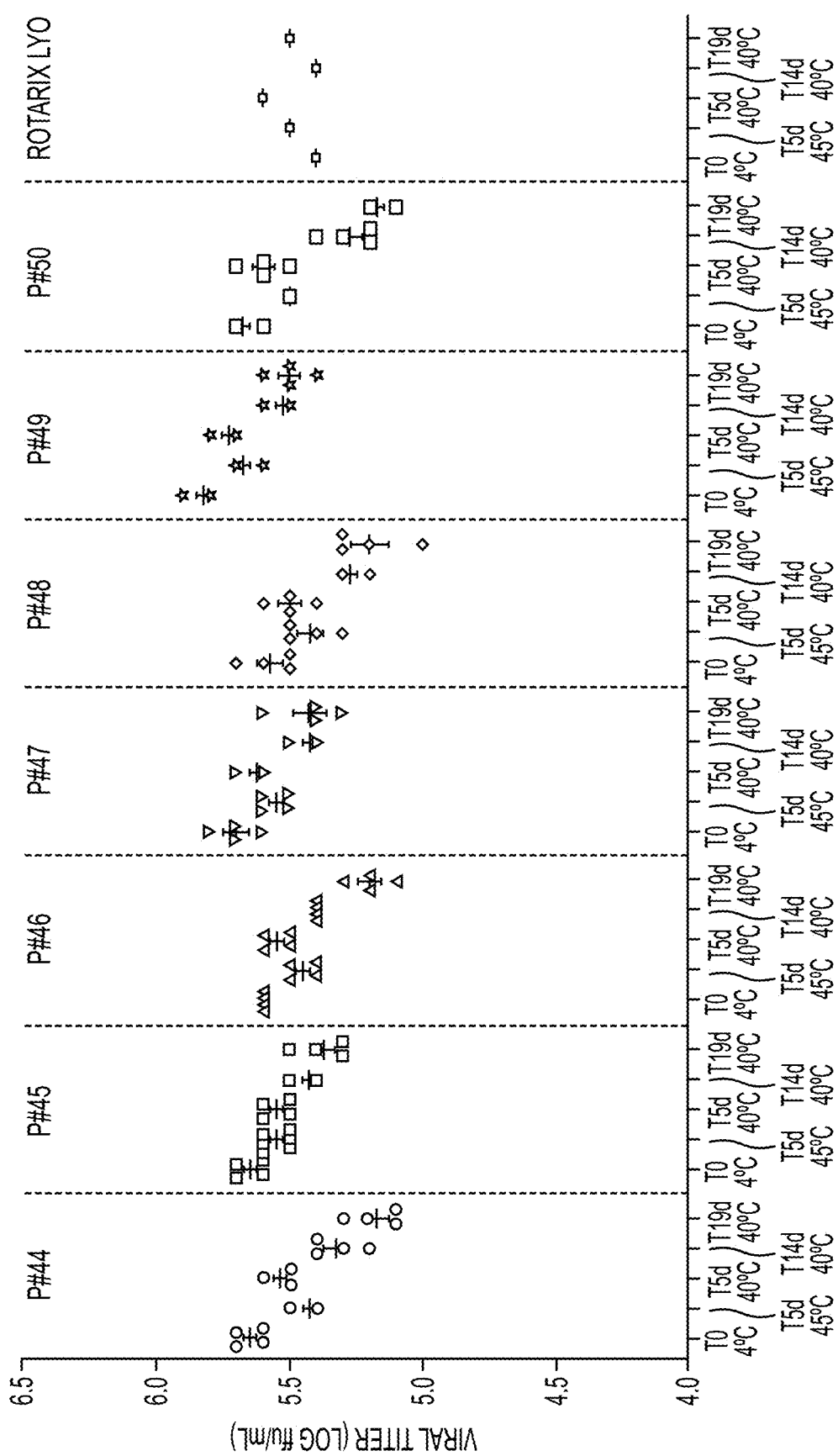
FIG. 2—Impact of divalent ions on thermostability. Viral titer ($Log_{10}$ ffu/mL, mean and standard deviation) at time points T0 4° C., T5 days 45° C., T5 days 40° C., T14 days 40° C. and T19 days 40° C. From left to right, formulations P #44 (no divalent ion), P #45 ($ZnCl_2$), P #46 ($CaCl_2$), P #47 ($ZnCl_2/CaCl_2$), P #48 ($MgCl_2$), P #49 ($MnCl_2$), P #50 (NaCl) and Rotarix lyo.

In a first aspect, the present invention provides a quick-dissolving thin film comprising a biological moiety and an excipient mix, wherein the excipient mix comprises
  one or more water-soluble polymer(s),
  a sugar selected from sucrose and trehalose,
  a metal ion,
  a carboxylate, and
  a buffering agent,
wherein said quick-dissolving thin film is thermostable.

In another aspect, the present invention provides a quick-dissolving thin film consisting of a biological moiety, an excipient mix, and optionally an antacid, wherein said excipient mix consists of
one or more water-soluble polymer(s),
a sugar selected from sucrose, trehalose and a combination thereof,
a metal ion,
a carboxylate,
a buffering agent,
optionally one or more amino acids,
wherein said quick-dissolving thin film is thermostable.

As used herein, a "quick-dissolving thin film" is a thin film that is suitable for administration to a mucosal surface of a patient and that dissolves rapidly upon contact with the mucosal surface. Typically, a "quick-dissolving thin film" comprises a water-soluble polymer matrix that rapidly dissolves on the mucosal surface, e.g. the tongue or buccal cavity, delivering the biological moiety to the digestive tract or to the systemic circulation. A quick-dissolving thin film of the invention can be used to administer the biological moiety via mucosal absorption. In a preferred embodiment, the quick-dissolving thin film is an oral thin film ("OTF") for administration in the mouth (buccally or sublingually). Quick dissolution and mucoadhesion are key properties important for patient compliance and improved administration of the biological moiety. Suitably, the quick-dissolving thin film dissolves quickly upon contact with mucosal tissue, in particular upon contact with saliva and buccal tissue in the case of an oral thin film, releasing the biological moiety. In a preferred embodiment, the quick-dissolving thin film dissolves in less than one minute, preferably in less than 50 seconds, upon contact with mucosal tissue, in particular upon contact with saliva and buccal tissue in the case of an oral thin film.

The quick-dissolving thin film of the invention comprises a biological moiety. The biological moiety can be selected from viruses, bacteria, proteins and nucleic acids. Examples of suitable biological moieties include a virus, a bacteria, a nucleic acid, a protein, an antibody, an enzyme, a growth factor, a cytokine or a virus-like particle.

In a preferred embodiment, the biological moiety is a virus. Suitably, the virus is selected from a live virus, a live attenuated virus and an inactivated virus.

A "live attenuated virus" is one that is viable (i.e. alive) but is either less virulent compared to the wild type strain or avirulent. Methods of attenuating viruses are known in the art, and include passaging in cell culture, preparing reassortant viruses, and using a variant from one species to vaccinate a subject of a different species. An "inactivated (or killed) virus" is one that is not viable. Methods of inactivating viruses are known in the art and are based on an inactivation step after incubation of infected cells (i.e. replication and propagation of the virus). A "live virus" is one that is viable and whose virulence has not been attenuated. The choice of a live, live attenuated or inactivated virus for the design of a vaccine will be dependent on whether the virus can cause a disease in the patient and on its level of virulence, and the immunogenicity of an attenuated, killed or live form.

In one embodiment, the virus is a reassortant virus. A "reassortant virus" is one that results from mixing of the genetic material of different viral strains. For example, at least one antigen or at least one segment of a first viral strain is replaced by at least one antigen or at least one segment of a second viral strain. Techniques for preparing reassortant viruses are well known in the art (See e.g. Foster, R. H and Wagstaff, A. J Tetravalent Rotavirus Vaccine, a review. ADIS drug evaluation, BioDrugs, Gev, 9 (2), 155-178, 1998 for reassortant rotaviruses).

In one embodiment, the virus is a live, live attenuated or inactivated virus which has been genetically modified to encode one or more antigens derived from a different pathogen which elicits a protective immune response against that pathogen.

The virus titer can be expressed in ffu (focus forming units) per ml or per dose. A suitable method for measuring the virus titer expressed in ffu per mL or per dose is as follows. Sample dilutions are inoculated on a cell lawn (for example MA-104 cells in the case of a rotavirus) for a time and temperature suitable to allow for a viral replication cycle (for example 16-18 hours at 37° C.±1° C. in the case of a rotavirus). Viral particles are revealed by immunostaining. After incubation, viral particles are detected by a monoclonal antibody specific to a viral antigen (e.g. 9F6 monoclonal antibody against VP4 in the case of a rotavirus) which is further revealed by a second antibody (anti-mouse) coupled with HRP (horseradish peroxidase) TrueBlue reagent is then added and turned into blue dots.

Alternatively, the virus titer can be expressed in CCID50 (Cell Culture Infectious Dose 50%) per ml or per dose. A suitable method for measuring the virus titer expressed in CCID50 per mL or per dose is as follows. Sample dilutions are inoculated on a cell lawn (for example MA-104 cells in the case of a rotavirus) for a time and temperature suitable to allow for a viral replication cycle (for example 7 days±1 day at 37° C.±1° C. in the case of a rotavirus). Viral particles are detected by immunofluorescence method. After incubation, infected cells come into contact with a monoclonal antibody against a viral antigen (e.g. 2C9 monoclonal antibody against VP7 in the case of a rotavirus) which is further revealed by a second antibody (anti-mouse) coupled with fluorescence molecule (FITC=Fluorescein IsoThioCyanate). Observation of fluorescent cells under the microscope indicates that the cell lawn was well infected by the virus. The viral titer is obtained by the Reed and Muench calculation method (Reed and Muench (1938) The American Journal of Hygiene 27:493-497).

Suitably, the virus is present in the quick-dissolving thin film of the invention at a titer ranging from about $1 \times 10^5$ to about $1 \times 10^{11}$ ffu per dose (or from about $1 \times 10^{5.5}$ to about $1 \times 10^{11.5}$ CCID50 per dose), more suitably at a titer ranging from about of $10^5$ to about $10^{10}$ ffu per dose (or from about $10^{5.5}$ to about $10^{10.5}$ CCID50 per dose).

In a preferred embodiment, the virus is a rotavirus.

Rotaviruses are non-enveloped icosahedral viruses with 11 segments of double stranded RNA encoding 6 structural (VP1-VP4, VP6, VP7) and 5 non-structural (NSP1-NSP5) proteins. With a diameter of about 100 nm, rotavirus is a complex macromolecular system composed of three concentric layers of proteins surrounding its genome. The innermost layer consists of 60 dimers of VP2 surrounding the viral genome and 12 copies each of the VP1 (RNA polymerase) and VP3 (guanyl transferase) proteins. The intermediate layer is composed of 260 trimers of VP6 with the external surface composed of 780 copies of the glycoprotein VP7 (260 trimers) and 60 spike-like structures of VP4 (dimers) which extend 12 nm from the surface. The VP6 protein determines the group and subgroup antigen, and VP4 and VP7 proteins are the determinants of serotype specificity. The glycoprotein VP7 defines G-types and the protease-sensitive protein VP4 defines P-types. Strains are generally designated by their G serotype specificities (e.g. serotypes G1 to G4 and G9), and the P-type is indicated by a number and a letter for the P-serotype and by a number in square brackets for the corresponding P-genotype. To date, at least 14 rotavirus G serotypes and 11 rotavirus P serotypes have been identified (Linhares A. C. & Bresse J. S., Pan. Am. J. Publ. Health 2000, 9, 305-330). Among these, 10 G serotypes and 6 P serotypes have been identified among the human rotaviruses (HRV).

In one embodiment, the quick-dissolving thin film of the invention comprises a live attenuated rotavirus, preferably a live attenuated human rotavirus (HRV), more preferably a live attenuated HRV selected from the group comprising serotypes G1, G2, G3, G4, G9, P[1] or P[8]. In a preferred embodiment, the rotavirus is a live attenuated human Rotavirus of a G1P[8] type. The quick-dissolving thin film of the invention may comprise more than 1 serotype of HRV and in a particular embodiment of the invention the HRV vaccine comprises 5 or more HRV serotypes (in particular G1, G2, G3, G4, G9, P1 or P8). In one embodiment, the rotavirus is a live attenuated human rotavirus selected from the 89-12C2 strain deposited with the ATCC (American Type Culture Collection, 12301 Parklawn Drive, Rockville, MD 20852) under accession VR 2272, its progeny, reassortants and immunologically active derivatives thereof, and the P43 strain deposited at the ECACC (European Collection of Animal Cell Cultures, Vaccine Research and Production Laboratory, Public Health Laboratory Service, Centre for Applied Microbiology and Research, Porton Down, Salisbury, Wiltshire, SP4 OJG, United Kingdom) on 13 Aug. 1999 under accession number ECACC 99081301, its progeny, reassortants and immunologically active derivatives thereof. Derivatives from deposited strains can be obtained by subjecting said strains to further processing such as by propagating them by further passaging, cloning, or other procedures using the live virus or by modifying said deposited strains in any way including by genetic engineering techniques or reassortant techniques. Such steps and techniques are well known in the art.

In another embodiment, the quick-dissolving thin film comprises a reassortant rotavirus, for example a human-human reassortant rotavirus, bovine-human reassortant rotavirus or a rhesus monkey-human reassortant rotavirus. Reassortant rotaviruses and techniques for preparing them are well known (Foster, R. H. and Wagstaff, A. J. Tetravalent Rotavirus Vaccine, a review. ADIS drug evaluation, BioDrugs, Gev, 9 (2), 155-178, 1998).

Rotaviruses may be produced according to routine production techniques. Typically, rotavirus preparations may be derived from tissue culture methods used to propagate the virus. Suitable cell substrates for growing the virus include for example dog kidney cells such as MDCK or cells from a clone of MDCK. MDCK-like cells, monkey kidney cells such as AGMK cells including Vero cells which are particularly suitable, other cells lines of monkey kidney origin such as BSC-1, LLC-MK2 and MA 104, suitable pig cell lines, or any other mammalian cell type suitable for the production of rotavirus for vaccine purposes. Suitable cell substrates also include human cells e.g. MRC-5 cells. Suitable cell substrates are not limited to cell lines, for example, primary cells are also included.

A rotavirus for inclusion in the quick-dissolving thin film of the invention can be monovalent, i.e. containing a single rotavirus strain, or be multivalent, i.e. containing at least two or more rotavirus strains.

Suitably the rotavirus is present in the quick-dissolving thin film of the invention at a titer ranging from about $1 \times 10^5$ to about $1 \times 10^8$ ffu per dose (or from about $1 \times 10^{5.5}$ to about $1 \times 10^{8.5}$ CCID50 per dose), more suitably at a titer ranging from about of $10^5$ to about $10^6$ ffu per dose (or from about $10^{5.5}$ to about $10^{6.5}$ CCID50 per dose).

The quick-dissolving thin film of the invention comprises an excipient mix comprising a water-soluble polymer, a sugar selected from sucrose and trehalose, a metal ion, a carboxylate and a buffering agent. The inventors have shown that such excipient mixes are suitable for providing thermostability to a biological moiety such as a virus in a quick-dissolving thin film in absence of an animal derived stabiliser such as gelatin.

The excipient mix comprises one or more water-soluble polymer(s). Suitable water-soluble polymers include polyvinyl alcohol (PVA), Polyethylene glycol (PEG), polyvinylpyrrolidone (PVP), alginate, croscarmellose sodium (also known as "carboxymethylcellulose sodium" or "sodium CMC") and hydroxypropyl methylcellulose (HPMC). Examples of suitable water-soluble polymer combinations include PVA-PEG (90%-10% by weight) and PVA-HPMC (90-10% by weight).

Suitably, the amount of the one or more water-soluble polymer(s) represents from about 30% to about 90% of the excipient mix by weight, preferably from about 40% to about 85% of the excipient mix by weight, for example about 40, 45, 50, 55, 60, 65, 70, 75, 80 or 85% of the excipient mix by weight.

In a preferred embodiment, the one or more water-soluble polymer(s) comprise PVA, suitably at least 80% PVA, more suitably at least 90% PVA.

In a more preferred embodiment, the excipient mix comprises a single water-soluble polymer which is PVA and the amount of PVA represents from about 30% to about 90% of the excipient mix by weight, preferably from about 40% to about 85% of the excipient mix by weight, for example about 40, 45, 50, 55, 60, 65, 70, 75, 80 or 85% of the excipient mix by weight.

The excipient mix comprises a sugar selected from sucrose, trehalose and a combination thereof. In a preferred embodiment the sugar is trehalose. In a more preferred embodiment, the sugar is trehalose dihydrate.

Suitably, the amount of the sugar represents from about 10% to about 60% of the excipient mix by weight, preferably from about 14% to about 45% of the excipient mix by weight, for example about 14, 15, 20, 25, 30, 35, 40, 42, or 45% of the excipient mix by weight. In a preferred embodiment, the sugar is trehalose (suitably trehalose dihydrate) and the amount of trehalose represents from about 10% to about 60% of the excipient mix by weight, preferably from about 14% to about 45% of the excipient mix by weight, for example about 14, 15, 20, 25, 30, 35, 40, 42, or 45% of the excipient mix by weight.

The excipient mix comprises a metal ion. Suitable metal ions include $Zn^{2+}$, $Ca^{2+}$, $Mg^{2+}$ and $Mn^{2+}$.

In one embodiment, the metal ion is selected from $Zn^{2+}$ and $Mn^{2+}$. In a preferred embodiment, the metal ion is $Zn^{2+}$. Suitably, the metal ion is in the form of a salt, preferably a chloride salt. In one embodiment, the metal ion is in the form of a chloride salt selected from $ZnCl_2$ and $MnCl_2$. In a preferred embodiment, the metal ion is in the form of $ZnCl_2$.

Suitably, the amount of the metal ion or salt represents from about 0.01% to about 1% of the excipient mix by weight, preferably from about 0.05% to about 0.5%, from about 0.08% to about 0.25%, from about 0.10% to about 0.20% of the excipient mix by weight, for example about 0.10, 0.11, 0.12, 0.13, 0.14, 0.15, 0.16, 0.17, 0.18, 0.19 or 0.20% of the excipient mix by weight. In a preferred embodiment, the metal ion is in the form of $ZnCl_2$ and the amount of $ZnCl_2$ represents from about 0.01% to about 1% of the excipient mix by weight, preferably from about 0.05% to about 0.5%, from about 0.08% to about 0.25%, from about 0.10% to about 0.20% of the excipient mix by weight, for example about 0.10, 0.11, 0.12, 0.13, 0.14, 0.15, 0.16, 0.17, 0.18, 0.19 or 0.20% of the excipient mix by weight.

The excipient mix comprises a carboxylate. Suitable carboxylates include succinate, citrate, fumarate, tartarate, maleate and lactate. In a preferred embodiment the carboxylate is citrate, suitably in the form of citrate acid.

Suitably, the amount of the carboxylate represents from about 0.5% to about 5% of the excipient mix by weight, preferably from about 0.75% to about 4%, from about 1% to about 3% of the excipient mix by weight, for example about 1, 1.5, 1.7, 1.75, 1.8, 1.85, 1.9, 2, 2.5 or 3% of the excipient mix by weight. In a preferred embodiment, the carboxylate is citric acid and the amount of citric acid represents from about 0.5% to about 5% of the excipient mix by weight, preferably from about 0.75% to about 4%, from about 1% to about 3% of the excipient mix by weight, for example about 1, 1.5, 1.7, 1.75, 1.8, 1.85, 1.9, 2, 2.5 or 3% of the excipient mix by weight.

The excipient mix comprises a buffering agent. In a preferred embodiment the buffering agent is selected from phosphate ($K_2HPO_4$) buffer and histidine base.

Suitably, the amount of the buffering agent represents from about 0.5% to about 5% of the excipient mix by weight, preferably from about 0.75% to about 4%, from about 1% to about 3% of the excipient mix by weight, for example about 1, 1.5, 1.7, 1.75, 1.8, 1.85, 1.9, 2, 2.5 or 3% of the excipient mix by weight. In a preferred embodiment, the buffering agent is selected from phosphate buffer and histidine base and the amount of phosphate buffer or histidine base represents from about 0.5% to about 5% of the excipient mix by weight, preferably from about 0.75% to about 4%, from about 1% to about 3% of the excipient mix by weight, for example about 1, 1.5, 1.7, 1.75, 1.8, 1.85, 1.9, 2, 2.5 or 3% of the excipient mix by weight.

In one embodiment, the excipient mix further comprises one or more amino acids. In a preferred embodiment, the one or amino acids are selected from glycine, arginine, proline, and combinations thereof. In a more preferred embodiment, the excipient mix comprises glycine, arginine or both.

Suitably, the amount of amino acids represents from about 0% to about 10% of the excipient mix by weight, preferably from about 0.05% to about 8%, from about 0.10% to about 7.5%, from about 0.15% to about 7% of the excipient mix by weight for example about 0.15, 0.20, 0.25, 0.50, 0.75, 1, 2, 3, 4, 5, 6 or 7% of the excipient mix by weight. In a preferred embodiment, the excipient mix comprises glycine, arginine or both, the amount of glycine represents from about 0% to about 5% of the excipient mix by weight, preferably from about 0.05% to about 4%, from about 0.08% to about 3% of the excipient mix by weight, for example about 0.08, 0.10, 0.15, 0.20, 0.25, 0.5, 0.75, 1, 1.5, 2, 2.5 or 3%% of the excipient mix by weight, and the amount of arginine represents from about 0% to about 10% of the excipient mix by weight, preferably from about 0.05% to about 8%, from about 0.10% to about 7.5%, from about 0.15% to about 7% of the excipient mix by weight, for example about 0.15, 0.20, 0.25, 0.50, 0.75, 1, 2, 3, 4, 5, 6 or 7% of the excipient mix by weight.

In one embodiment of the quick-dissolving thin film of die invention, the biological moiety is a virus, which is present in the quick-dissolving thin film of the invention at a titer ranging from about $1\times10^5$ to about $1\times10^{11}$ ffu per dose, and wherein the excipient mix comprises or consists of

- between 30% and 90%, preferably between 40% and 85%, for example about 40, 45, 50, 55, 60, 65, 70, 75, 80 or 85% by weight of the one or more water-soluble polymer,
- between 10% and 60%, preferably between 14% and 45%, for example about 14, 15, 20, 25, 30, 35, 40, 42, or 45% by weight of sucrose and/or trehalose,
- between 0.01% and 1%, preferably between 0.05% and 0.5%, between 0.08% and 0.25%, between 0.10% and 0.20%, for example about 0.10, 0.11, 0.12, 0.13, 0.14, 0.15, 0.16, 0.17, 0.18, 0.19 or 0.20% by weight of the metal ion or salt,
- between 0.5% and 5%, preferably between 0.75% and 4%, between 1% and 3%, for example about 1, 1.5, 1.7, 1.75, 1.8, 1.85, 1.9, 2, 2.5 or 3% by weight of the carboxylate,
- between 0.5% and 5%, preferably between 0.75% and 4%, between 1% and 3%, for example about 1, 1.5, 1.7, 1.75, 1.8, 1.85, 1.9, 2, 2.5 or 3% by weight of the buffering agent, and
- between 0% and 20%, preferably between 0.05% and 15%, between 0.05% and 12%, between 0.05% and 10%, for example about 0.05, 0.10, 0.15, 0.20, 0.25, 0.50, 0.75, 1, 2, 3, 4, 5, 6, 7, 8, 9 or 10% by weight of one or more amino acids.

In a preferred embodiment of the quick-dissolving thin film of the invention, the biological moiety is a virus, and wherein in the excipient mix,

- the water-soluble polymer is PVA,
- the sugar is trehalose,
- the metal ion is in the form of $ZnCl_2$,
- the carboxylate is citric acid,
- the buffering agent is selected from of $K_2HPO_4$ and histidine base, and
- the one or more amino acids, if present, are selected from arginine and/or glycine.

In a more preferred embodiment of the quick-dissolving thin film of the invention, the excipient mix comprises or consists of

- between 30% and 90%, preferably between 40% and 85%, for example about 40, 45, 50, 55, 60, 65, 70, 75, 80 or 85% by weight of PVA,
- between 10% and 60%, preferably between 14% and 45%, for example about 14, 15, 20, 25, 30, 35, 40, 42, or 45% by weight of trehalose,
- between 0.01% and 1%, preferably between 0.05% and 0.5%, between 0.08% and 0.25%, between 0.10% and 0.20%, for example about 0.10, 0.11, 0.12, 0.13, 0.14, 0.15, 0.16, 0.17, 0.18, 0.19 or 0.20% by weight of $ZnCl_2$,
- between 0.5% and 5%, preferably between 0.75% and 4%, between 1% and 3%, for example about 1, 1.5, 1.7, 1.75, 1.8, 1.85, 1.9, 2, 2.5 or 3% by weight of citric acid,
- between 0.5% and 5%, preferably between 0.75% and 4%, between 1% and 3%, for example about 1, 1.5, 1.7, 1.75, 1.8, 1.85, 1.9, 2, 2.5 or 3% by weight of $K_2HPO_4$ or histidine base,
- between 0% and 10%, preferably between 0.05% and 8%, between 0.10% and 7.5%, between 0.15% and 7%, for example about 0.15, 0.20, 0.25, 0.50, 0.75, 1, 2, 3, 4, 5, 6 or 7% by weight of arginine and,
- between 0% and 5%, preferably between 0.05% and 4%, between 0.08% and 3%, for example about 0.08, 0.10, 0.15, 0.20, 0.25, 0.5, 0.75, 1, 1.5, 2, 2.5 or 3% by weight of glycine.

Preferably, the virus is a rotavirus. Suitably, the rotavirus is present in the quick-dissolving thin film of the invention at a titer ranging from about $1\times10^5$ to about $1\times10^8$ ffu per dose.

In a preferred embodiment, the quick-dissolving thin film further comprises an antacid. Indeed, drugs delivered through the gastrointestinal (GI) tract are subjected to low pH (high acidity) and harsh enzymatic environment in the gastric cavity. Biological moieties can be denatured or degraded by such conditions leading to significant loss in their bioactivity. Antacids can be used to prevent such denaturation and degradation when the biological is administered orally Herein, an "antacid" is a compound that allows to increase stomach pH for a time sufficiently long for the biological to pass through the stomach without being significantly affected. Antacid capacity can be measured by the Baby Rossett-Rice (BBR) test as described below in example 1(2), FIG. 1. In a preferred embodiment, the antacid allows the pH to remain above 4 in the BBR test for at least 10 minutes, preferably for at least 15 minutes.

Suitable antacids include alkaline acetate, citrate, succinate, tartrate, maleate, lactate, ammonium bicarbonate, phosphate, magnesium oxide, aluminum oxide, aluminium hydroxide with magnesium hydroxide, aluminum carbonate gel, calcium carbonate, sodium bicarbonate, hydrotalcite, sucralfate, bismuth subsalicylate, adipate such as sodium adipate, and/or the like. In a preferred embodiment, the antacid is calcium carbonate ($CaCO_3$).

In a preferred embodiment of the quick-dissolving thin film of the invention, the biological moiety is a virus, for example a rotavirus, and the quick-dissolving thin film further comprises an antacid which is calcium carbonate.

In one embodiment, the quick-dissolving thin film of the invention further comprises an antacid and the excipient mix:antacid ratio (w/w) is from about 1:3 to about 2:1, from about 1:2 to 1.5:1, from about 1:1.5 to 1:1, for example about 1:1.5, 1:1.4, 1:1.3, 1:1.2, 1:1.1 or 1:1. In a preferred embodiment, the quick-dissolving thin film of the invention further comprises an antacid which is $CaCO_3$, and the excipient mix:$CaCO_3$ ratio (w/w) is from about 1:3 to about 2:1, from about 1:2 to 1.5:1, from about 1:1.5 to 1:1, for example about 1:1.5, 1:1.4, 1:1.3, 1:1.2, 1:1.1 or 1:1.

In a preferred embodiment of the quick-dissolving thin film of the invention, the biological moiety is a rotavirus, which is present in the quick-dissolving thin film of the invention at a titer ranging from about $1\times10^5$ to about $1\times10^8$ ffu per dose, and the excipient mix comprises or consists of
between 40% and 85%, for example about 40, 45, 50, 55, 60, 65, 70, 75, 80 or 85% by weight of PVA,
between 14% and 45%, for example about 14, 15, 20, 25, 30, 35, 40, 42, or 45% by weight of trehalose,
between 0.10% and 0.20%, for example about 0.10, 0.11, 0.12, 0.13, 0.14, 0.15, 0.16, 0.17, 0.18, 0.19 or 0.20% by weight of $ZnCl_2$,
between 0.5% and 5%, preferably between 0.75% and 4%, between 1% and 3%, for example about 1, 1.5, 1.7, 1.75, 1.8, 1.85, 1.9, 2, 2.5 or 3% by weight of the citric acid,
between 1% and 3%, for example about 1, 1.5, 1.7, 1.75, 1.8, 1.85, 1.9, 2, 2.5 or 3% by weight of a buffering agent selected from phosphate ($K_2HPO_4$) buffer or histidine base,
between 3% and 7.5%, for example about 3, 3.5, 4, 4.5, 5, 5.5, 6, 6.5, 7 or 7.5% by weight of arginine and,
between 1% and 4%, for example about 1, 1.5, 2, 2.5, 3, 3.4 or 4% by weight of glycine, and said quick-dissolving thin film comprises an antacid which is $CaCO_3$, and the excipient mix:$CaCO_3$ ratio (w/w) is from about 1:3 to about 1:1, for example about 1:3, 1:2, 1:1.5 or 1:1.

Suitably, the quick-dissolving thin film of the invention has a surface pH between 5 and 9. Herein, "surface pH" refers to the pH at the surface of the quick-dissolving thin film surface. Methods for measuring surface pH will be known to the person skilled in the art. For example, a small volume of aqueous solution (e.g. 20-25 µl) can be placed on the surface of the quick-dissolving thin film and left to soak for about 5 minutes. pH (litmus) paper is then placed on the dampened surface and the pH is read according to the pH paper indication.

Suitably the surface pH of the quick-dissolving thin film should be close to physiological pH in order to avoid irritation of the mucosa. The surface pH should also be such as not to destabilise the biological moiety. Suitably, the quick-dissolving thin film has a surface pH between 5 and 9, preferably between 5.5 and 8, more preferably between 6.0 and 7.5, for example 6.0, 6.1, 6.2, 6.3, 6.4, 6.5, 6.6, 6.7, 6.8, 6.9, 7.0, 7.1, 7.2, 7.3, 7.4 or 7.5.

The quick-dissolving thin film of the invention is thermostable.

The thermostability of a quick-dissolving thin film of the invention may be assessed by measuring the virus titer of the composition at T0, storing the quick-dissolving thin film at a set temperature for a set period of time, and measuring the virus titer loss after storage relative to the virus titer at T0. Thus, as used herein, stability of a quick-dissolving thin film refers to its ability to resist to a decrease in viral titer over time, and thermostability refers to the ability to resist to a decrease in viral titer due to exposure to temperatures above 2-8° C. (non-refrigerated temperatures).

Suitably, the quick-dissolving thin film of the invention is stable for 2 years at 20° C., preferably for 2 years at 25° C., more preferably for 2 years at 30° C.

In one embodiment of the quick-dissolving thin film of the invention, the biological moiety is a virus and the quick-dissolving thin film has a maximum virus titer loss of 0.5, more preferably 0.4, more preferably still 0.3 log 10 ffu per dose, after storage for 2 years at 20° C. In a preferred embodiment of the quick-dissolving thin film of the invention, the biological moiety is a virus and the quick-dissolving thin film has a maximum virus titer loss of 0.5, more preferably 0.4, more preferably still 0.3 log 10 ffu per dose, after storage for 2 years at 25° C. In a still more preferred embodiment of the quick-dissolving thin film of the invention, the biological moiety is a virus and the quick-dissolving thin film has a maximum virus titer loss of 0.5, more preferably 0.4, more preferably still 0.3 log 10 ffu per dose, after storage for 2 years at 30° C.

A predictive model, for example a model derived from the Arrhenius model (Egan, W., & Schofield, T. (2009). Basic principles of stability. Biologicals, 37(6), 379-386.) based on an accelerated degradation scheme, can be used to estimate long term stability at a given temperature T (for example 20° C., 25° C. or 30 °C. depending on the geographic area for which the thermostable thin film is intended). Such models are well known in the art and rely on the extrapolation of stability data obtained over a shorter period of time at higher temperatures in order to predict long term stability at temperature T.

In a preferred embodiment, the quick-dissolving thin film of the invention is stable for at least 5 weeks at 40° C. In one embodiment of the quick-dissolving thin film of the invention, the biological moiety is a virus and the quick-dissolving thin film has a maximum virus titer loss of 0.5 log 10 ffu per dose after storage for 5 weeks at 40° C. In a preferred embodiment of the quick-dissolving thin film of the invention, the biological moiety is a virus and the quick-dissolving thin film has a maximum virus titer loss of 0.4 log 10 ffu per dose after storage for 5 weeks at 40° C. In a more preferred embodiment of the quick-dissolving thin film of the invention, the biological moiety is a virus and the quick-dissolving thin film has a maximum virus titer loss of 0.3 log 10 ffu per dose after storage for 5 weeks at 40° C. In a yet a more preferred embodiment of the quick-dissolving thin film of the invention, the biological moiety is a virus and the quick-dissolving thin film has a maximum virus titer loss of 0.2 log 10 ffu per dose after storage for 5 weeks at 40° C.

In another preferred embodiment, the quick-dissolving thin film of the invention is stable for at least 10 weeks at 40° C. In one embodiment of the quick-dissolving thin film of the invention, the biological moiety is a virus and the quick-dissolving thin film has a maximum virus titer loss of 1, more suitably of 0.9, 0.8, 0.7, 0.6, 0.5 or 0.4 log 10 ffu per dose after storage for 10 weeks at 40° C. In a preferred embodiment of the quick-dissolving thin film of the invention, the biological moiety is a virus and the quick-dissolving thin film has a maximum virus titer loss of 0.6 log 10 ffu per dose after storage for 10 weeks at 40° C. In a more preferred embodiment of the quick-dissolving thin film of the invention, the biological moiety is a virus and the quick-dissolving thin film has a maximum virus titer loss of 0.5 log 10 ffu per dose after storage for 10 weeks at 40° C. In a yet a more preferred embodiment of the quick-dissolving thin film of the invention, the biological moiety is a virus and the quick-dissolving thin film has a maximum virus titer loss of 0.4 log 10 ffu per dose after storage for 10 weeks at 40° C.

In another embodiment, the biological moiety is a virus and the quick-dissolving thin film has a maximum virus titer loss of 0.5 CCID50 per dose after storage for 5 weeks at 40° C. In a preferred embodiment of the quick-dissolving thin film of the invention, the biological moiety is a virus and the quick-dissolving thin film has a maximum virus titer loss of 0.4 CCID50 per dose after storage for 5 weeks at 40° C. In a more preferred embodiment of the quick-dissolving thin film of the invention, the biological moiety is a virus and the quick-dissolving thin film has a maximum virus titer loss of 0.3 CCID50 per dose after storage for 5 weeks at 40° C. In a yet a more preferred embodiment of the quick-dissolving thin film of the invention, the biological moiety is a virus and the quick-dissolving thin film has a maximum virus titer loss of 0.2 CCID50 per dose after storage for 5 weeks at 40° C.

In another embodiment of the quick-dissolving thin film of the invention, the biological moiety is a virus and the quick-dissolving thin film has a maximum virus titer loss of 1, more suitably of 0.9, 0.8, 0.7, 0.6, 0.5 or 0.4 CCID50 per dose after storage for 10 weeks at 40° C. In a preferred embodiment of the quick-dissolving thin film of the invention, the biological moiety is a virus and the quick-dissolving thin film has a maximum virus titer loss of 0.6 CCID50 per dose after storage for 10 weeks at 40° C. In a more preferred embodiment of the quick-dissolving thin film of the invention, the biological moiety is a virus and the quick-dissolving thin film has a maximum virus titer loss of 0.5 CCID50 per dose after storage for 10 weeks at 40° C. In a yet a more preferred embodiment of the quick-dissolving thin film of the invention, the biological moiety is a virus and the quick-dissolving thin film has a maximum virus titer loss of 0.4 CCID50 per dose after storage for 10 weeks at 40° C.

In a preferred embodiment, the quick-dissolving thin film of the invention does not comprise any animal derived product.

In a preferred embodiment, the quick-dissolving thin film of the invention does not comprise gelatin.

In a preferred embodiment, the quick-dissolving thin film of the invention does not comprise albumin.

In a preferred embodiment, the quick-dissolving thin film of the invention is suitable for administration to a human patient. Suitably, the human patient is selected from an adult, a child and an infant.

In a preferred embodiment, the quick-dissolving thin film of the invention is suitable for oral administration to a human patient. Suitably, the human patient is selected from an adult, a child and an infant.

In a preferred embodiment, the quick-dissolving thin film of the invention has a dissolution time of less than 1 minute, preferably less than 50 seconds. As used herein, "dissolution time" refers to the time required at a given temperature, suitably at 37° C., for the thin film to completely dissolve when put in contact with a wet surface such as water or saliva. Methods for measuring a dissolution time are known in the art. For example, the dissolution time of a quick dissolving thin film of the invention can be assessed by using the method explained below in Example 1(5).

In a preferred embodiment, the quick-dissolving thin film of the invention has thickness of less than 500 µm, preferably less than 400 µm, more preferably less than 300 µm, more preferably still, less than 250 µm.

In a preferred embodiment, the quick-dissolving thin film of the invention has a surface between 300 and 600 mm$^2$, preferably between 400 and 500 mm$^2$.

Quick-dissolving thin film that are flexible, or partly flexible (flex/brit) are preferred over brittle quick-dissolving thin films. The flexibility/brittleness of a quick-dissolving thin film can be assessed as described in Example 1(7) below.

The moisture content (or residual humidity) of a quick-dissolving thin film can be measured as described in Example 1(3) below. A lower moisture content (residual humidity) is thought to be associated with a higher thermo-stability of the quick-dissolving thin film. However, a very low moisture content may render the quick-dissolving thin film more brittle. It is hypothesized that excipients such as trehalose and amino acids, in particular glycine or arginine, enhance thermostability, thus allowing for a higher moisture content.

In a preferred embodiment, the quick-dissolving thin film of the invention has a moisture content between 2 and 10% by weight, more suitably between 3 and 8%, for example, about 3%, 4%, 5%, 6%, 7% or 8% by weight. In a preferred embodiment, the moisture content is lower than about 9, 8, 7, 6 or 5% by weight.

Suitably, when the quick-dissolving thin film comprises an antacid, the quick-dissolving thin film of the invention has a moisture content between 2 and 10% by weight on an antacid-free basis, more suitably between 3 and 8%, for example, about 3%, 4%, 5%, 6%, 7% or 8% by weight on an antacid-free basis. In a preferred embodiment, the moisture content is lower than about 9, 8, 7, 6 or 5% by weight on an antacid-free basis.

The quick-dissolving thin films of the present invention are suitable for use in therapy and in particular for use in the prevention and/or treatment of disease in a mammal or a bird, and in particular in a human.

In a preferred embodiment of the quick-dissolving thin film of the invention, the biological moiety is immunogenic.

More preferably, the quick-dissolving thin film is suitable for use as a vaccine. As used herein, a vaccine refers to an immunogenic composition capable, after a suitable dosing regime in a subject, of eliciting an immune response in that subject specific to an antigen contained in the vaccine. A vaccine will reduce the occurrence or incidence of infection and/or disease (specific to the vaccine's target pathogen) in an appropriately treated population.

In one aspect, the present invention provides a quick-dissolving thin film of the invention for use in therapy.

In a further aspect, the present invention provides a quick-dissolving thin film of the invention for use in the prevention or treatment of an infectious disease in a subject.

In a further aspect, the invention provides the use of a quick-dissolving thin film of the invention in the manufacture of a medicament for use in the treatment or prevention of an infectious disease in a subject.

In a further aspect, the invention provides a method for the treatment or prevention of an infectious disease in a subject comprising administering a quick-dissolving thin film of the invention to a subject.

Suitably, in the therapeutic uses and methods of the invention, the subject is a mammal or a bird. In a preferred embodiment, the subject is a human, for example an infant, a child or an adult.

Suitably, in the therapeutic uses and methods of the invention, the quick-dissolving thin film is an oral thin film for oral administration to a human, for example an infant, a child or an adult.

Suitably, in the therapeutic uses and methods of the invention, the quick-dissolving thin film may be given several times to the subject over a period of time, for example twice or three times over a period of one to six months. Typically, each dose will be given to the subject at a one or two month interval.

Suitably, in the therapeutic uses and methods of the invention, the infectious disease is caused by a rotavirus and the quick-dissolving thin film comprises a biological moiety which is a rotavirus. In particular, the rotavirus quick-dissolving thin film can be used to prevent and/or treat rotavirus-associated gastro-enteritis. In a preferred embodiment, the rotavirus quick-dissolving thin film is for administration to human infants at risk of an infection by a rotavirus. More preferably, the rotavirus quick-dissolving thin film is an oral thin film for oral administration to human infants at risk of an infection by a rotavirus.

Suitably the rotavirus is present in the quick-dissolving thin film of the invention at a titer ranging from about $1 \times 10^5$ to about $1 \times 10^8$ ffu per dose (or from about $1 \times 10^{5.5}$ to about $1 \times 10^{8.5}$ CCID50 per dose), more suitably at a titer ranging from about of $10^5$ to about $10^6$ ffu per dose (or from about $10^{5.5}$ to about $10^{6.5}$ CCID50 per dose).

In a further aspect, the present invention provides a kit comprising the quick-dissolving thin film of the invention in a sterile packaging and instructions for use of the kit.

In a further aspect, the invention provides a method for preparing a thermostable quick-dissolving thin film comprising a biological moiety, comprising the steps of:
 a) preparing an aqueous solution comprising or consisting of
  a biological moiety,
  one or more water-soluble polymer(s),
  a sugar selected from sucrose, trehalose and a combination thereof,
  a metal ion,
  a carboxylate, and
  one or more buffering agents,
 b) adjusting the pH of the aqueous solution to a value comprised between 5 and 9,
 c) applying the aqueous solution on a drying surface,
 d) drying the aqueous solution to obtain a thin film, and
 e) removing the dried thin film from the drying surface, thereby obtaining said thermostable quick-dissolving thin film.

The drying surface in step c) is typically a planar surface. The aqueous solution can be applied and allowed to spread seeking the lowest level by gravity on a level horizontal drying surface. The aqueous solution can be sprayed, painted or spread evenly with a casting knife, e.g., uniformly onto the drying surface. The drying surface can alternately not be planar and/or horizontal. For example, the drying surface can be a drum, or the wet blend could be extruded vertically to dry, e.g., as a tape. In any case, it is usually desired to present a large surface relative to volume, to speed drying or allow for less stressful drying conditions. In one embodiment, the aqueous solution is applied to a broad planar surface and exposed to heat from above (e.g., warm gas stream and/or IR light) and/or from below with the drying surface itself being heated.

In step d), following exposure to heated drying, additional moisture can be removed from the aqueous solution by vacuum drying.

Suitably, the duration and temperature of the drying step d) are selected such as to obtain a quick-dissolving thin film which has a moisture content lower than about 10% by weight. In a preferred embodiment, the moisture content is lower than about 9, 8, 7, 6 or 5% by weight.

Suitably, the volume of the aqueous solution and size of the drying surface in step c), and the duration and temperature of the drying step d) are selected such as to obtain a quick-dissolving thin film which has a thickness of less than 500 μm, preferably less than 400 μm, more preferably less than 300 μm, more preferably still, less than 250 μm.

Typically, the drying temperature in step d) is from about 50° C. to about 90° C., for example from about 55° C. to about 70° C., for example 60° C. or 65° C. Suitably, the duration of the drying step d) is from about 30 to about 180 minutes, for example from about 40 to about 120 or about 50 to about 90 minutes, for example 50, 55, 60, 65, 70, 75, 80, 85 or 90 minutes.

In one embodiment, step e) is followed by a step f) of cutting the dried thin film into quick-dissolving thin films which have a surface between 300 and 600 mm², preferably between 400 and 500 mm².

The aqueous solution of step a) comprises a biological moiety. Suitably, the biological moiety is selected from viruses, bacteria, proteins and nucleic acids. Examples of suitable biological moieties include a virus, a bacteria, a nucleic acid, a protein, an antibody, an enzyme, a growth factor, a cytokine or a virus-like particle. In a preferred embodiment, the biological moiety is a virus. Suitably, the virus is selected from a live virus, a live attenuated virus and an inactivated virus. In one embodiment, the virus is a reassortant virus. In one embodiment, the virus is a live or live attenuated virus which has been genetically modified to encode one or more antigens derived from a different pathogen which elicits a protective immune response against that pathogen. Suitably, the virus is present in the aqueous solution at a titer ranging from about $1 \times 10^5$ to about $1 \times 10^{11}$ ffu per ml (or from about $1 \times 10^{5.5}$ to about $1 \times 10^{11.5}$, CCID50 per ml), more suitably at a titer ranging from about of $10^5$ to about $10^{10}$ ffu per ml (or from about $10^{5.5}$ to about $10^{10.5}$ CCID50 per ml).

In a preferred embodiment, the aqueous solution of step a) comprises a biological moiety which is a rotavirus. In one embodiment, the aqueous solution comprises a live attenuated rotavirus, preferably a live attenuated human rotavirus (HRV), more preferably a live attenuated HRV selected from the group comprising serotypes G1, G2, G3, G4, G9, P[1] or P[8]. In a preferred embodiment, the rotavirus is a live attenuated human Rotavirus of a G1P[8] type. The aqueous solution may comprise more than 1 serotype of HRV and in a particular embodiment of the invention the HRV vaccine comprises 5 or more HRV serotypes (in particular G1, G2, G3, G4, G9, P1 or P8). In one embodiment, the rotavirus is a live attenuated human rotavirus selected from the 89-12C2 strain deposited with the ATCC (American Type Culture Collection, 12301 Parklawn Drive, Rockville, MD 20852) under accession VR 2272, its progeny, reassortants and immunologically active derivatives thereof, and the P43 strain deposited at the ECACC (European Collection of Animal Cell Cultures, Vaccine Research and Production Laboratory, Public Health Laboratory Service, Centre for Applied Microbiology and Research, Porton Down, Salisbury, Wiltshire, SP4 OJG, United Kingdom) on 13 Aug. 1999 under accession number ECACC 99081301, its progeny, reassortants and immunologically active derivatives thereof. In another embodiment, the aqueous solution comprises a reassortant rotavirus, for example a human-human reassortant rotavirus, bovine-human reassortant rotavirus or a rhesus monkey-human reassortant rotavirus. A rotavirus for inclusion in the aqueous solution can be monovalent, i.e. containing a single rotavirus strain, or be multivalent, i.e. containing at least two or more rotavirus strains. Suitably the rotavirus is present in the aqueous solution at a titer ranging from about $1 \times 10^5$ to about $1 \times 10^8$ ffu per ml (or from about $1 \times 10^{5.5}$ to about $1 \times 10^{8.5}$ CCID50 per ml), more suitably at a titer ranging from about of $10^5$ to about $10^6$ ffu per ml (or from about $10^{5.5}$ to about $10^{6.5}$ CCID50 per ml).

The aqueous solution of step a) comprises one or more water-soluble polymer(s). Suitable water-soluble polymers include polyvinyl alcohol (PVA), Polyethylene glycol (PEG), polyvinylpyrrolidone (PVP), alginate, croscarmellose sodium (also known as "carboxymethylcellulose sodium" or "sodium CMC") and hydroxypropyl methylcellulose (HPMC). Examples of suitable water-soluble polymer combinations include PVA-PEG (90%-10% by weight) and PVA-HPMC (90%-10% by weight).

Suitably, the concentration of the one or more water-soluble polymer in the aqueous solution of step a) is from about 5% to about 30% (w/v), preferably from about 8% to about 20% (w/v), for example about 8, 9, 10, 11, 12, 13, 14, 15, 16, 17, 18, 19 or 20% (w/v).

Suitably, the one or more water-soluble polymers in the aqueous solution of step a) comprise PVA, suitably at least 80% PVA, more suitably at least 90% PVA.

In a preferred embodiment, the aqueous solution of step a) comprises a single water-soluble polymer which is PVA, and the concentration of PVA in the aqueous solution of step a) is from about 5% to about 30% (w/v), preferably from about 8% to about 20% (w/v), for example about 8, 9, 10, 11, 12, 13, 14, 15, 16, 17, 18, 19 or 20% (w/v).

The aqueous solution of step a) comprises a sugar selected from sucrose, trehalose and a combination thereof. In a preferred embodiment the sugar is trehalose. In a more preferred embodiment, the sugar is trehalose dihydrate.

Suitably, the concentration of the sugar in the aqueous solution of step a) is from about 1% to about 15% (w/v), preferably from about 1.5% to about 10% (w/v), for example about 1.5, 2, 3, 4, 5, 6, 7, 8, 9 or 10% (w/v). In a preferred embodiment, the sugar is trehalose (suitably trehalose dihydrate) and the concentration of trehalose in the aqueous solution of step a) is from about 1% to about 15% (w/v), preferably from about 1.5% to about 10% (w/v), for example about 1.5, 2, 3, 4, 5, 6, 7, 8, 9 or 10% (w/v) The aqueous solution of step a) comprises a metal ion. Suitable metal ions include $Zn^{2+}$, $Ca^{2+}$, $Mg^{2+}$ and $Mn^{2+}$. In one embodiment, the metal ion is selected from $Zn^{2+}$ and $Mn^{2+}$. In a preferred embodiment, the metal ion is $Zn^{2+}$. Suitably, the metal ion is in the form of a salt, preferably a chloride salt. In one embodiment, the metal ion is in the form of a chloride salt selected from $ZnCl_2$ and $MnCl_2$. In a preferred embodiment, the metal ion is in the form of $ZnCl_2$.

Suitably, the concentration of the metal ion or salt in the aqueous solution of step a) is from about 0.005% to about 0.5% (w/v), preferably from about 0.01% to about 0.10%, from about 0.015 to about 0.05%, for example about 0.015, 0.02, 0.03, 0.04 or 0.05, 3, 4, 5, 6, 7, 8, 9 or 10 mM % (w:v). In a preferred embodiment, the metal ion is in the form of $ZnCl_2$ and the concentration of $ZnCl_2$ in the aqueous solution of step a) is from about 0.005% to about 0.5% (w/v), preferably from about 0.01% to about 0.10%, from about 0.015 to about 0.05%, for example about 0.015, 0.02, 0.03, 0.04 or 0.05% (w:v).

The aqueous solution of step a) comprises a carboxylate. In a preferred embodiment the carboxylate is citric acid.

Suitably, the concentration of the carboxylate in the aqueous solution of step a) is from about 0.05% to about 1% (w/v), preferably from about 0.1% to about 0.8%, for example about 0.1, 0.2, 0.3, 0.4, 0.5, 0.6, 0.7 or 0.8% (w/v). In a preferred embodiment, the carboxylate is citric acid and the concentration of citric acid in the aqueous solution of step a) is from about 0.05% to about 1% (w/v), preferably from about 0.1% to about 0.8%, for example about 0.1, 0.2, 0.3, 0.4, 0.5, 0.6, 0.7 or 0.8% (w/v).

The aqueous solution of step a) comprises one or more buffering agents. In a preferred embodiment the buffering agent is selected from phosphate ($K_2HPO_4$) buffer and histidine base.

Suitably, the concentration of the buffering agent(s) in the aqueous solution of step a) is from about 0.05% to about 1% (w/v), preferably from about 0.1% to about 0.8%, for example about 0.1, 0.2, 0.3, 0.4, 0.5, 0.6, 0.7 or 0.8% (w/v). In a preferred embodiment, the buffering agent is selected from phosphate buffer and histidine base and the concentration of phosphate buffer or histidine base in the aqueous solution of step a) is from about 0.05% to about 1% (w/v), preferably from about 0.1% to about 0.8%, for example about 0.1, 0.2, 0.3, 0.4, 0.5, 0.6, 0.7 or 0.8% (w/v).

In one embodiment of the method of the invention, the aqueous solution of step a) further comprises one or more amino acids. In a preferred embodiment, the one or amino acids are selected from glycine, arginine, proline, and combinations thereof. In a more preferred embodiment, the excipient mix comprises glycine, arginine or both.

Suitably, the concentration of amino acid(s) in the aqueous solution of step a) is from about 0 to about 2% (w/v), preferably from about 0.01% to about 1.5%, from about 0.015% to about 1.2%, for example about 0.015, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1 or 1.2% (w/v).

In a preferred embodiment, the aqueous solution of step a) comprises glycine, arginine or both. In a preferred embodiment, the aqueous solution of step a) comprises glycine at a concentration from about 0 to about 1% (w/v), preferably from about 0.005% to about 1%, from about 0.01% to about 0.5%, for example about 0.01, 0.015, 0.02, 0.025, 0.03, 0.04, 0.05, 0.06, 0.07, 0.08, 0.09, 0.10, 0.20, 0.30, 0.40 or 0.50% (w/v), and arginine at a concentration from about 0 to about 2% (w/v), preferably from about 0.01% to about 1.5%, from about 0.02% to about 1%, for example about 0.02, 0.03, 0.04, 0.05, 0.06, 0.07, 0.08, 0.09, 0.10, 0.20, 0.30, 0.40, 0.50, 0.60, 0.70, 0.80, 0.90 or 1% (w/v).

In one embodiment of the method of the invention, an antacid is added to the aqueous solution of step a). In a preferred embodiment, the antacid allows the pH to remain above 4 in the BBR test for at least 10 minutes, preferably for at least 15 minutes. Suitable antacids include alkaline acetate, citrate, succinate, tartrate, maleate, lactate, ammonium bicarbonate, phosphate, magnesium oxide, aluminum oxide, aluminium hydroxide with magnesium hydroxide, aluminum carbonate gel, calcium carbonate, sodium bicarbonate, hydrotalcite, sucralfate, bismuth subsalicylate, and/or the like. In a preferred embodiment, the antacid is calcium carbonate ($CaCO_3$). In a preferred embodiment of the method of the invention, the aqueous solution of step a) comprises a biological moiety which is a virus, for example a rotavirus, and further comprises an antacid which is calcium carbonate.

Suitably, the aqueous solution of step a) comprises an antacid at a concentration from about 10 to about 50% (w/v), preferably from about 15 to 40% (w/v), for example about 15, 20, 25, 30, 35 or 40% (w/v). In a preferred embodiment, the antacid is calcium carbonate and the concentration of calcium carbonate in the aqueous solution of step a) is from about 10 to about 50% (w/v), preferably from about 15 to 40% (w/v), for example about 15, 20, 25, 30, 35 or 40% (w/v).

In step b), the pH is adjusted to a value comprised between about 5 and about 9, preferably between about 6 and about 8, for example about 6, 6.5, 7, 7.5 or 8. Suitably, KOH and/HCl is used to adjust the pH in step b).

In a preferred embodiment, the aqueous solution of step a) does not comprise any animal derived product. In a preferred embodiment, the aqueous solution of step a) does not comprise gelatin. In a preferred embodiment, the aqueous solution of step a) does not comprise albumin.

In a further aspect, the invention provides a thermostable quick-dissolving thin film obtainable by the method of the invention.

In a preferred embodiment of the quick-dissolving thin film of the invention, the biological moiety is a virus, for example a rotavirus, and the quick-dissolving thin film has a maximum virus titer loss of 1, more suitably of 0.9, 0.8, 0.7, 0.6, 0.5, 0.4, 0.3 log 10 ffu per dose after storage for 10 weeks at 40° C. In another embodiment of the quick-dissolving thin film of the invention, the biological moiety is a virus and the quick-dissolving thin film has a maximum virus titer loss of 1, more suitably of 0.9, 0.8, 0.7, 0.6, 0.5, 0.4, 0.3 CCID50 per dose after storage for 10 weeks at 40° C.

The subject matter of and information disclosed within the publications and patents or patent applications mentioned in this specification are hereby incorporated by reference in their entirety.

The terms "comprising", "comprise" and "comprises" herein are intended by the inventors to be optionally substitutable with the terms "consisting of", "consist of" and "consists of", respectively, in every instance.

The term "about" in relation to a numerical value x means x±5% or 10%.

The invention will now be described further by way of reference to the following, non-limiting examples.

EXAMPLES

Example 1—Methods (1) Rotavirus oral thin film (OTF) manufacture—Aqueous excipient stock solutions were aseptically formulated with pH adjusted to 6.5 with 10 N KOH. An equal volume of a 25% (w/v) polymer stock solution was also prepared. These excipient stock solutions were first aseptically combined with $CaCO_3$ powder (average particle size 30 micron) to target a 24.3% by weight loading in the final film wet blend mixing on a magnetic stir plate at an approximately speed of 100 rpm for 5-10 minutes, which dispersed the powder evenly. Then the 25% (w/v) polymer stock solution was aseptically added into the mixture and continued to mix for another 10-15 minutes until homogenous. 10N KOH or 6N HCl were used to adjust the pH of the final film wet blend to a value between 6.5 and 7.5. Lastly, a 10× concentrated bulk rotavirus vaccine was aseptically added to the mixture and gently stirred at a speed of 80-100 rpm for additional 5 minutes. The film wet blend was degassed by letting it sit at room temperature for 5-10 minutes. The resulting rotavirus film wet blend was cast on a polyethylene terephthalate (PET) backing liner (Kinmar PET, K-Mac Plastic) using a manual applicator (BYK-Gardner) at a depth of 30 mil. The wet films were dried for 35 to 90 minutes at 65° C. in a convection oven (VWR, model 1350FM).

(2) Antacid capacity—Baby Rossett-Rice (BBR) testing—The system used for the BBR testing is represented on FIG. 1. Water for injection (WFI) was added to the formulation in a beaker (50 ml) in order to obtain a final liquid volume of ten (10) ml. The beaker was then installed in a water bath adjusted to obtain 37° C. inside the beaker. The sample of antacid was added to the beaker. Measurement of pH value represents the "initial pH". Then 4 ml of 0.1 N HCl is added at once and at the same time the clock and the pump are started. The pump will continuously add 0.5 ml/min of 0.1N HCl, pH values are recorded along the time, until pH 4 is obtained.

(3) Residual humidity (or Moisture content) testing—The goal of this test was to measure trace quantities of water within the OTF by the colorimetric titration process using an organic solvent (Hydranal Coulamat AG) to extract water from the sample. A known amount of OTF sample and Hydranal are placed in a serum glass vial. The solvent/film is allowed to mix for thirty (30) minutes to extract water from the sample. A known amount of hydranal (extracted from the sample) is then injected to the Karl Fisher titrator to measure the amount of water present in the sample. The overall moisture content (MC) of the OTF is then calculated based on the calculated Mass Fraction of solvent, solids in samples, and solvent in sample. To determine the moisture content on a $CaCO_3$-free basis, the overall OTF moisture content is divided by the mass fraction of non-CaCO3 components in the dry film.

(4) Infectivity Testing

OTF reconstitution: Based on the weight of the OTF, the reconstitution volume was determined by calculation to reach a final concentration of rotavirus of 6.3 $\log_{10}$ CCID50/ml (corresponding to the current Rotarix lyo formulation containing 6.5 $\log_{10}$ CCID50 per 1.5 ml oral vaccine). Each OTF was then inserted in a 4.5 ml vial containing DMEM or WFI at its reconstitution volume. The sample was cut in 3 pieces with a pair of scissors and all the pieces were inserted with tweezers in the vial.

In vitro infectivity test: After viral activation by trypsin, optimal sample dilutions were added to previously seeded MA-104 cells for 16-18 hours at 37° C.±1° C. to allow for a viral replication cycle. After incubation, infected cells were detected using the rotavirus VP4-specific monoclonal antibody 9F6 of which the binding was revealed using a HRP-conjugated anti-mouse antibody followed by incubation with the Trueblue reagent. The viral titer was obtained by counting the blue dots, and was expressed as $\log_{10}$ FFU/dose or/ml. The cut-off was set at 3.9 $\log_{10}$ ffu/mL (limit of detection). For the purpose of the analysis, all values below the cut-off were arbitrary set at 3.6 $\log_{10}$ ffu/mL.

(5) Dissolution time—The method to measure dissolution time was adapted from USP (United States Pharmacopeia) chapter <711>. Briefly, a Paddle Apparatus Type 2 was used to measure OTF dissolution time. Briefly, a water bath maintained temperature inside the media vessel at 37° C. This temperature was controlled by a heating device with a temperature probe placed inside the vessel. The distance between the bottom of the impeller blade and the inside bottom of the vessel was approximately 25 mm and was maintained fixed during testing. The vessel is cylindrical with a flat bottom and volumetric capacity of 1 liter. About 300 ml of media (PBS (1×): 137 mM NaCl, 2.7 mM KCl, 10 mM $Na_3PO_4$—isotonic) was used for the dissolution test. The shaft position was within 2 mm of the vertical axis of the vessel; rotation was smooth without significant wobble during testing. A spiral "sinker" held the OTF in place at the bottom of the media vessel during the test. Rotation speed of approximately 65 rpm was controlled by a stirrer controller.

(6) Surface pH—A small volume of aqueous solution (20-25 ul) was placed on the OTF, soaking for 5 minutes before placing pH (litmus) paper on the dampened surface. The pH was read according to the pH paper indication.

(7) Flexibility/brittleness—A 20 mm×20 mm film was sectioned from the film strip, the sectioned film was then folded top to bottom using tweezers to determine the flexibility and brittleness of sample. If the sample did not break into two pieces without cracks visible this was considered a flexible film. If a crack was seen but no separation seen this was considered flexible/brittle. If film sample broke into two pieces, then it was considered brittle.

(8) Statistical methods—SAS 9.4 software was used to evaluate the slopes (decay by unit time) through a simple linear model using on the log 10 transformed titer assumed to be normally distributed with unknown variance with the day as fixed effect factor. Mean loss for each time point with 95% CI are derived from Least square mean difference in the model with timepoint as covariable.

Example 2—Thermostability of Rotavirus OTF Formulations with Different Divalent Ions OTF batches P #44 to P #50 were prepared as described in Example 1(1). Prior to combining with the CaCO3 and PVA stock solution (25% PVA w/v), the excipient stock solution comprised 20% (w/v) sucrose, 41.6 mM citric acid, 50 mM $K_2PO_4$, and optionally one or more (two) divalent ions:

Formulation P #44: none
Formulation P #45: 4 mM $ZnCl_2$
Formulation P #46: 4 mM $CaCl_2$
Formulation P #47: 4 mM $ZnCl_2$/4 mM $CaCl_2$
Formulation P #48: 4 mM $MgCl_2$
Formulation P #49: 4 mM $MnCl_2$
Formulation P #50: 50 mM NaCl The final pH of each wet blend solution was adjusted to 6.5. The drying time was set to 90 minutes for all batches. After drying, each OTF batch comprised about 59% (w/w) of $CaCO_3$ and about 41% (w/w) of the combined excipient/polymer mix, and the excipient/polymer mix (on a $CaCO_3$-free basis) consisted of 53.2-53.5% (w/w) of polyvinyl alcohol (PVA), 42.5-42.8% (w/w) of sucrose, 1.9% (w/w) of $K_2HPO_4$, 1.9% (w/w) of Citric Acid and 0.12-0.62% divalent ion (when present).

The thermostability of each OTF batch was assessed by determining the viral titer at time points T0 4° C., T5 days 45° C., T5 days 40° C., T14 days 40° C. and T19 days 40° C. as described in Example 1(4) above. Four samples were tested at each timepoint. Rotarix lyo (commercial vaccine) was also tested as a control. The results are presented in FIG. 2.

Example 3—Model for Estimating Long Term Stability Based on the Arrhenius Model A base formulation P #51 was used for the Arrhenius model. OTF batch P #51 was prepared as described in Example 1(1). Prior to combining with the $CaCO_3$ and PVA stock solution (25% PVA w/v), the excipient stock solution comprised 20% (w/v) sucrose, 41.6 mM citric acid and 50 mM $K_2PO_4$. The final pH of the wet blend solution was adjusted to 6.5. The drying time was set to 90 minutes. After drying, OTF batch P #51 comprised about 59% (w/w) of $CaCO_3$ and about 41% (w/w) of the combined excipient/polymer mix, and the excipient/polymer mix (on a $CaCO_3$-free basis) consisted of 53.5% (w/w) of polyvinyl alcohol (PVA), 42.8% (w/w) of sucrose, 1.9% (w/w) of $K_2HPO_4$, and 1.9% (w/w) of Citric Acid.

The thermostability of OTF batch P #51 was assessed by determining the viral titer at time points T0 4° C., T70 days 30° C., T26 days 40° C. and T5 days 45° C. as described in Example 1(4) above. Four samples were tested at each timepoint. The individual results were in Table 1.

TABLE 1

Thermostability data of OTF batch p#51

| ID | Temp | Timepoint (days) | Viral_titer_log_ffu_per_mL |
|---|---|---|---|
| P#51 OTF 30 | 40° C. | 26 | 5.4485 |
| P#51 OTF 15 | 40° C. | 26 | 5.0603 |
| P#51 OTF 16 | 40° C. | 26 | 5.1913 |
| P#51 OTF 23 | 40° C. | 26 | 5.4832 |
| P#51 OTF 12 | 45° C. | 5 | 5.7521 |
| P#51 OTF 3 | 45° C. | 5 | 5.6918 |
| P#51 OTF 8 | 45° C. | 5 | 5.7660 |
| P#51 OTF 29 | 45° C. | 5 | 5.6618 |
| P#51 OTF 31 | 30° C. | 70 | 5.6703 |
| P#51 OTF 19 | 30° C. | 70 | 5.7122 |
| P#51 OTF 9 | 30° C. | 70 | 5.7309 |
| P#51 OTF 27 | 30° C. | 70 | 5.7267 |
| P#51 OTF 7 | 4° C. | T0 | 5.9139 |
| P#51 OTF 28 | 4° C. | T0 | 5.8970 |
| P#51 OTF 10 | 4° C. | T0 | 5.9146 |
| P#51 OTF 20 | 4° C. | T0 | 5.8038 |

Based on the assumption that the simplest plausible kinetic model for vaccine degradation would be one based on first order kinetics, the least square estimate for the degradation rate (or slope) for each combination of time-point and temperature were estimated using a simple linear regression model (with intercept) on the $\log_{10}$ transformed titer with the day as fixed effect factor (proc glm SAS 9.4).

The following Fixed Effect model has been applied for each temperature.

$$\text{Potency}=\log_{10}(Y)=\beta_0+\beta_{1T}\text{Day}+\varepsilon$$

where Y is the vector of viral titer measurements (mean ffu/mL)

$\beta_0$=mean log titer at Day 0

$\beta_{1T}$=slope or degradation rate of log titer by time unit (day) at temperature T $\varepsilon$ vector of random error, independent, identically and normally distributed with a mean of zero and a standard deviation of $\sigma^2$ Once the degradation rates were estimated at each temperature T (see Table 2), and on the assumption that the loss in the log titer remains linear, estimates of the unknown parameters in the Arrhenius Equation were obtained by fitting a linear regression model to the logarithm of the estimated degradation rates ($-\beta_{1T}$) ($K_T$ in the Arrhenius Equation with the inverse of temperature (in Kelvin) as the fixed factor). This model assumes that the degradation rate $K_T$ is function of temperature T: a higher temperature T leads to a larger $K_T$ or faster degradation.

TABLE 2

Degradation rate by day for each temperature condition

| Temperature in ° C. | Temperature in ° K. | Degradation rate by log ffu per day $(-\beta 1)=K_T$ |
|---|---|---|
| 30° C. | 303 | 0.00246 |
| 40° C. | 313 | 0.02256 |
| 45° C. | 318 | 0.03288 |

Note:
the intercept ($\beta 0$) is 5.8823. Temperature in Kelvin = Temperature in Celsius + 273

Estimates of the unknown parameters in the Arrhenius Equation were obtained from the following linear model $$\text{Ln}(K_T)=\ln(A)+(\alpha)*(1/T)$$

where
 $K_T$ is the degradation rate (in $\log_{10}$ viral titer per day) at temperature T (in ° K.) obtained from the linear regression on the $\log_{10}$ titer at temperature T
 $\ln(A)$ is the intercept
 ($\alpha$) is the slope of the regression line of $\ln(K_T)$ versus $1/T$
 T is the temperature (in ° K).

Figure 3A:
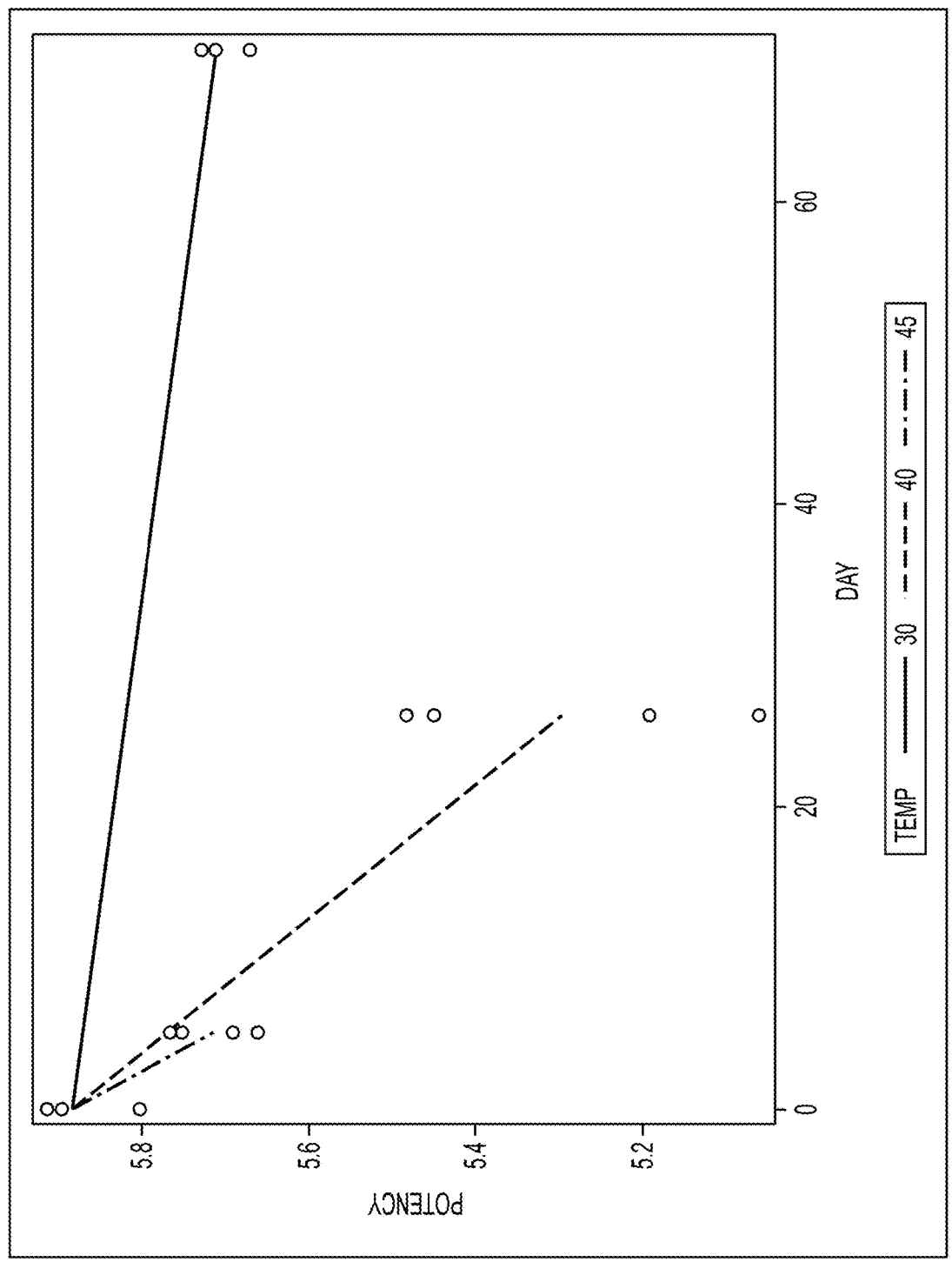
FIG. 3—Degradation rate by temperature for P #51 expressed in $log_{10}$ ffu/mL (FIG. 3A) and as ln(degradation rate expressed in $log_{10}$ ffu/mL per day) (FIG. 3B).
Figure 3B:
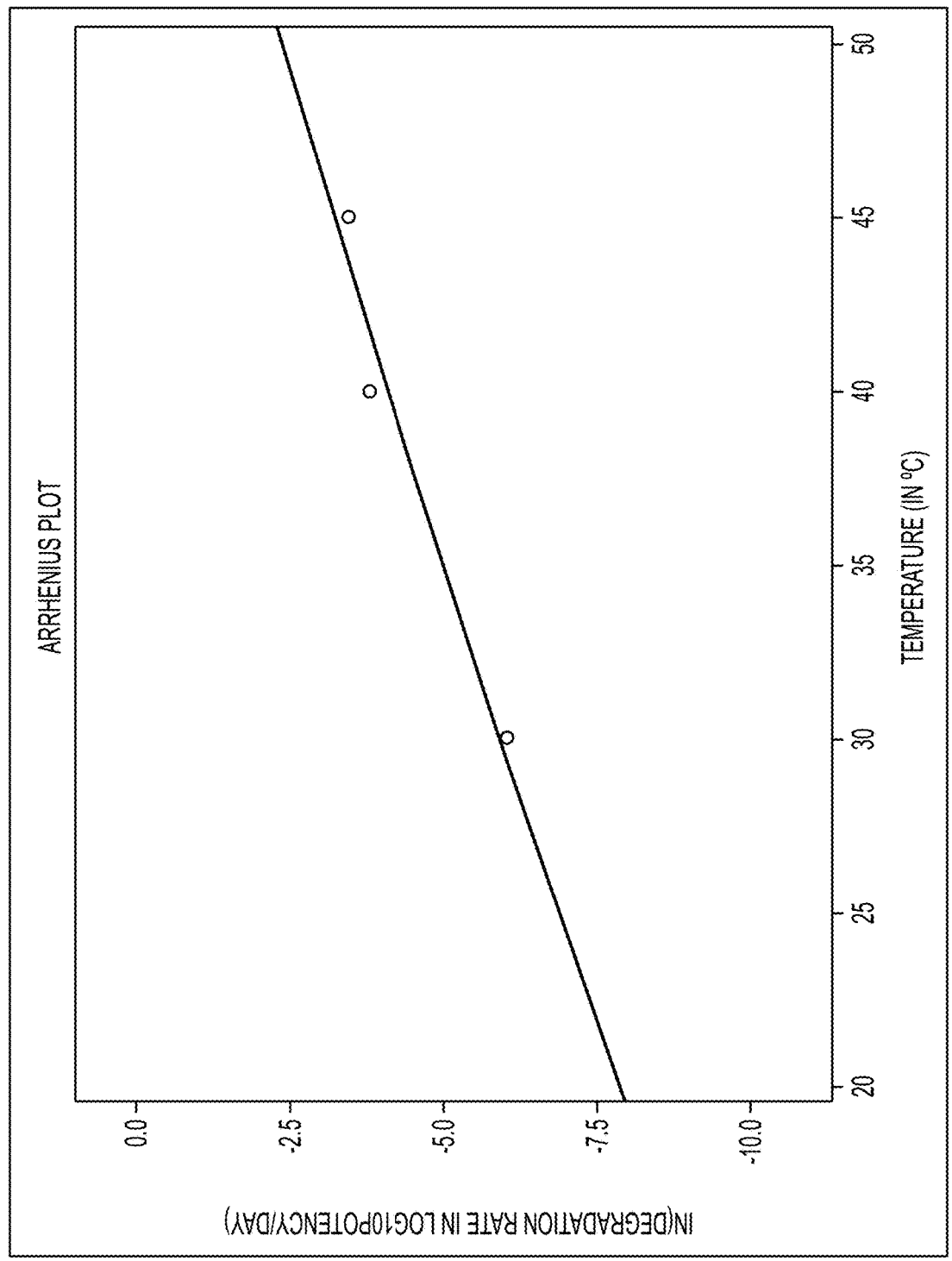

The illustration of the degradation rates by temperature are shown in FIG. 3.

Example 4—Thermostability of Rotavirus OTF Formulations with Different Excipients OTF batches P #58 to P #70 were prepared as described in Example 1(1). Prior to combining with the CaCO3 and PVA stock solution (25% PVA w/v), the excipient stock solution comprised 20% (w/v) sucrose, 41.6 mM citric acid, 50 mM $K_2PO_4$, 4 mM $ZnCl_2$ and optionally an additional excipient as follow:
Formulation P #58: none
Formulation P #59: 25 mM histidine
Formulation P #60: 25 mM arginine
Formulation P #61: 25 mM methionine
Formulation P #62: 25 mM proline
Formulation P #63: 25 mM hydroxyproline
Formulation P #64: none
Formulation P #65: 25 mM glycine
Formulation P #66: 25 mM glutamic acid
Formulation P #67: 0.4% (w/v) travasol (on a solids basis)
Formulation P #68: 25 mM alanine
Formulation P #69: 0.2% (w/v) rHSA
Formulation P #70: 0.5% (w/v) sorbitol
Travasol is a 10% (w/v) mix of amino acids comprising:

| | mg/100 mL |
|---|---|
| alanine | 2070 |
| glycine | 1030 |
| arginine | 1150 |
| proline | 680 |
| leucine | 730 |
| valine | 580 |
| serine | 500 |
| isoleucine | 600 |
| threonine | 420 |
| phenylalanine | 560 |
| lysine-hydrochloride | 580 |
| histidine | 480 |
| methionine | 400 |
| tryptophan | 180 |
| tyrosine | 40 |
| acetate | 88 mEq |
| chloride | 40 mEq |

The final pH of each wet blend solution was adjusted to 6.5. The drying time was set to 90 minutes for all batches. After drying, each OTF batch comprised about 59% (w/w) of $CaCO_3$ and about 41% (w/w) of the combined excipient/polymer (PVA) mix.

Figure 4:
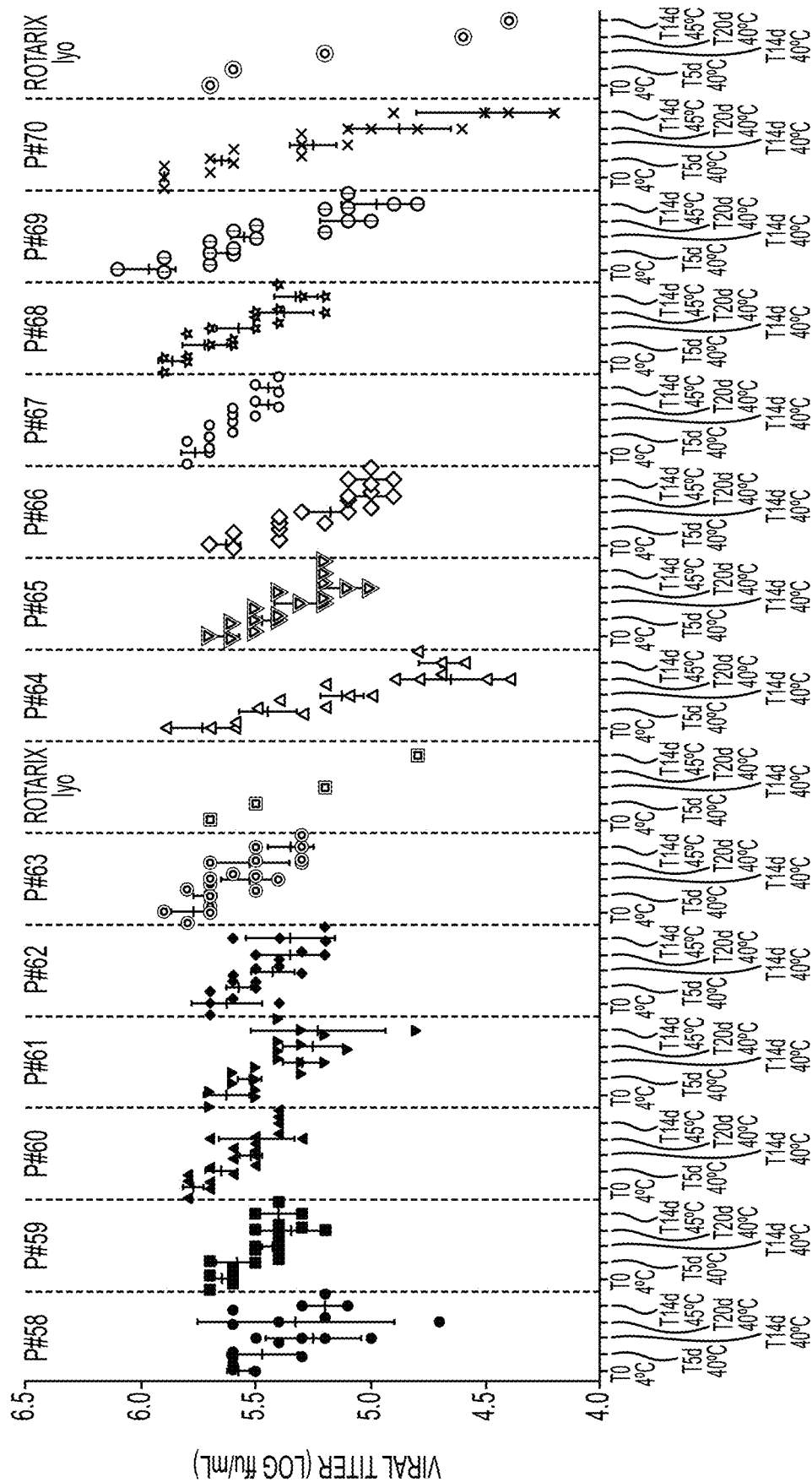
FIG. 4—Impact of excipients on thermostability. Viral titer ($Log_{10}$ ffu/mL, mean and standard deviation) at time points T0 4° C., T5 days 40° C., T14 days 40° C., T20 days 40° C. and T14 days 45° C. From left to right, formulations P #58 ($ZnCl_2$), P #59 ($ZnCl_2$+histidine), P #60 ($ZnCl_2$+arginine); P #61 ($ZnCl_2$+methionine), P #62 ($ZnCl_2$+proline), P #63 ($ZnCl_2$+hydroxypoline), Rotarix lyo, P #64 ($ZnCl_2$), P #65 ($ZnCl_2$+glycine), P #66 ($ZnCl_2$+glutamic acid), P #67 ($ZnCl_2$+travasol), P #68 ($ZnCl_2$+alanine), P #69 ($ZnCl_2$+rHSA), P #70 ($ZnCl_2$+sorbitol) and Rotarix lyo.

The thermostability of each OTF batch was then assessed by determining the viral titer at time points T0 4° C., T5 days 40° C., T14 days 40° C., T20 days 40° C. and T14 days 45° C. as described in Example 1(4) above. Four samples were tested at each timepoint. Rotarix lyo (commercial vaccine) was also tested as a control. Formulations P #58 to P #63 were tested in a first round, and formulations P #64 to P #70 were tested in a second round. The results are presented in FIG. 4.

Example 5—Thermostability of Rotavirus OTF Formulations with Different Excipients OTF batches P #71 to P #77 were prepared as described in Example 1(1). Prior to combining with the CaCO3 and PVA stock solution (25% PVA w/v), the excipient stock solution comprised 20% (w/v) sucrose (with the exception of P #74), 41.6 mM citric acid, 50 mM $K_2PO_4$, 4 mM $ZnCl_2$ and optionally an additional excipient as follow:
Formulation P #71: none
Formulation P #72: 25 mM phenylalanine
Formulation P #73: 0.5% (w/v) glycerol
Formulation P #74: 20% (w/v) trehalose dihydrate (replacing sucrose)
Formulation P #75: 0.1% (w/v) TPGS (D-α-Tocopherol polyethylene glycol 1000 succinate, a water-soluble form of Vitamin E)
Formulation P #76: 0.1% (w/v) Polysorbate 20
Formulation P #77: 0.1% (w/v) Pluronic F68
The final pH of each wet blend solution was adjusted to 6.5. The drying time was set to 90 minutes for all batches.

After drying, each OTF batch comprised about 59% (w/w) of CaCO₃ and about 41% (w/w) of excipient/polymer (PVA) mix.

Figure 5:
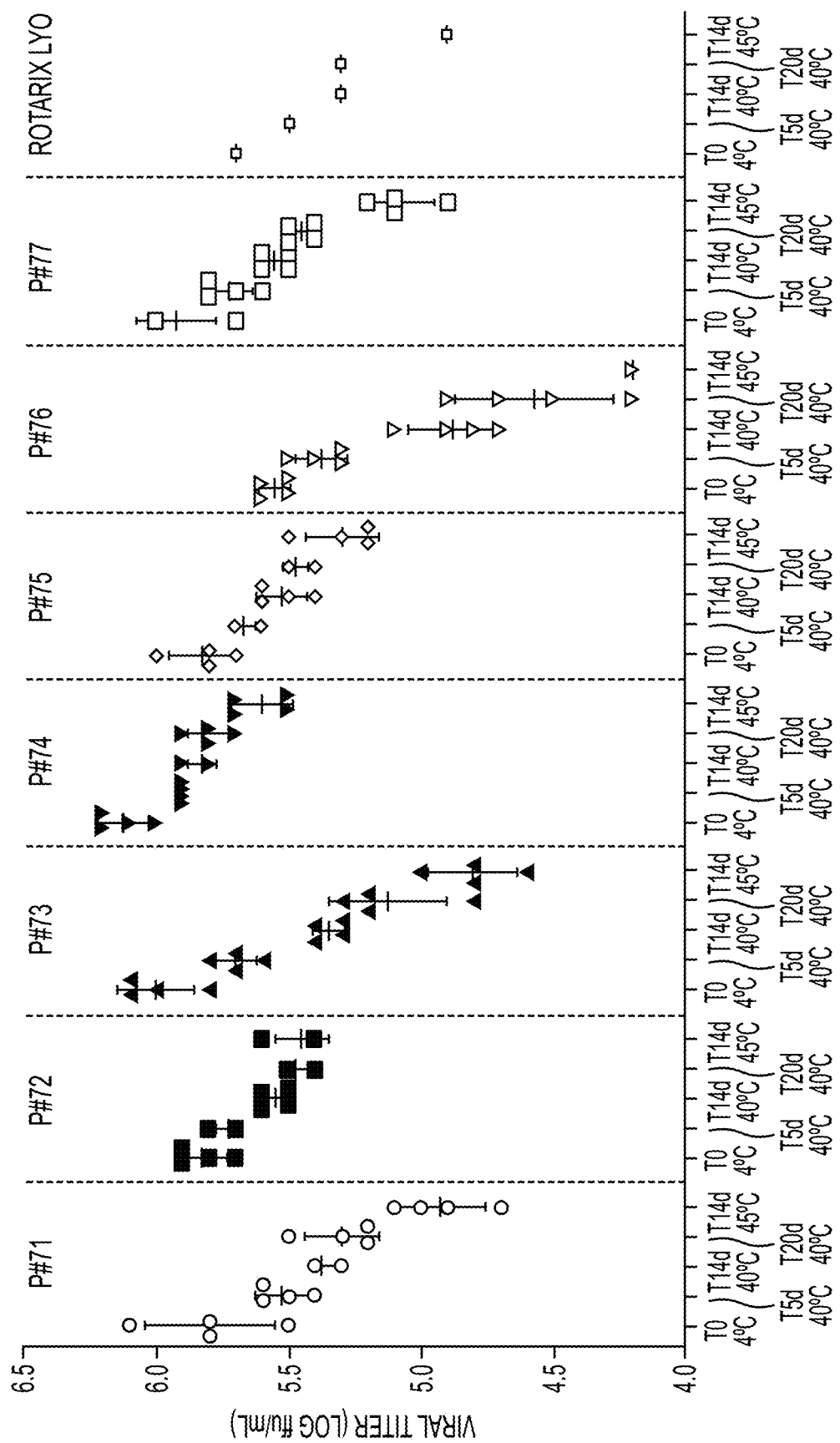
FIG. 5—Impact of excipients on thermostability. Viral titer ($Log_{10}$ ffu/mL, mean and standard deviation) at time points T0 4° C., T5 days 40° C., T14 days 40° C., T20 days 40° C. and T14 days 45° C. From left to right, formulations P #71 ($ZnCl_2$), P #72 ($ZnCl_2$+phenylalanine), P #73 ($ZnCl_2$+glycerol), P #74 ($ZnCl_2$+trehalose), P #75 ($ZnCl_2$+TPGS), P #76 ($ZnCl_2$+Polysorbate20), P #77 ($ZnCl_2$+Pluronic F68) and Rotarix lyo.

The thermostability of each OTF batch was assessed by determining the viral titer at time points T0 4° C., T5 days 40° C., T14 days 40° C., T20 days 40° C. and T14 days 45° C. as described in Example 1(4) above. Four samples were tested at each timepoint. Rotarix lyo (commercial vaccine) was also tested as a control. The results are presented in FIG. 5.

Example 6. Thermostability of Rotavirus OTF Formulations with Different Buffers and pH OTF batches P #84 to P #89 were prepared as described in Example 1(1). Prior to combining with the CaCO3 and PVA stock solution (25% PVA w/v), the excipient stock solution comprised 20% (w/v) sucrose, 41.6 mM citric acid, 4 mM $ZnCl_2$ and a buffer selected from 50 mM $K_2PO_4$ and 50 mM histidine buffer and the pH was adjusted as follow:
Formulation P #84: 50 mM $K_2PO_4$ buffer, pH 6.5
Formulation P #85: 50 mM $K_2PO_4$ buffer, pH 7
Formulation P #86: 50 mM $K_2PO_4$ buffer, pH 7.5
Formulation P #87: 50 mM histidine buffer, pH 6.5
Formulation P #88: 50 mM histidine buffer, pH 7
Formulation P #89: 50 mM histidine buffer, pH 7.5

The drying time was set to 90 minutes for all batches. After drying, each OTF batch comprised about 59% (w/w) of CaCO₃ and about 41% (w/w) of excipient/polymer (PVA) mix.

Figure 6:
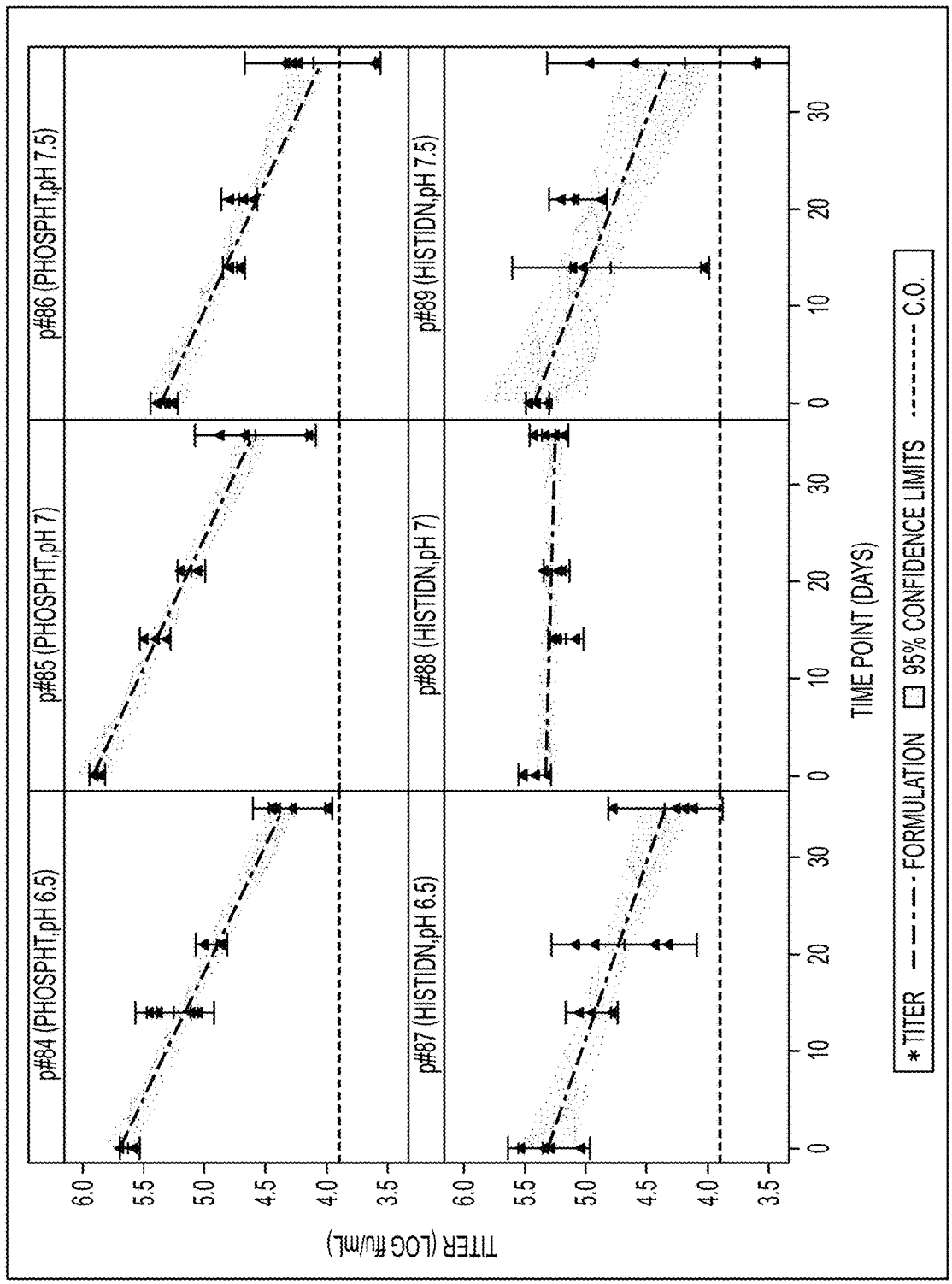
FIG. 6—Thermostability of OTF batches P #84, P #85, P #86, P #87, P #88 and P #89. Viral titer ($Log_{10}$ ffu/mL, mean and 95% confidence limits) at time points T0 4° C., T2 weeks 40° C., T3 weeks 40° C. and T5 weeks 40° C.

The thermostability of each OTF batch was assessed by determining the viral titer at time points T0 4° C., T2 weeks 40° C., T3 weeks 40° C. and T5 weeks 40° C. as described in Example 1(4) above. Four samples were tested at each timepoint. The results are presented in FIG. 6.

Example 7—Thermostability of Rotavirus OTF Formulations with Different Polymers OTF batches P #94, P #95, P #97 and P #100 were prepared as described in Example 1(1). Prior to combining with the CaCO3 and polymer stock solution (25% polymer w/v), the excipient solution comprised 20% (w/v) sucrose, 41.6 mM citric acid, 50 mM $K_2PO_4$, 4 mM $ZnCl_2$. The 25 wt % polymer stock solutions had the following composition:
Formulation P #94: PVA/PEG400 (90%/10% w/w)
Formulation P #95: PVA/HPMC (90%/10% w/w)
Formulation P #97: PVA (100%)
Formulation P #100: PVP/PEG400 (90%/10% w/w)

The final pH of each wet blend solution was adjusted to 6.5. The drying time was set to 90 minutes for formulations P #94 and P #97, 65 minutes for P #95 and 35 minutes for P #100. After drying, each OTF batch comprised about 59% (w/w) of CaCO₃ and about 41% (w/w) of excipient/polymer mix.

Figure 7:
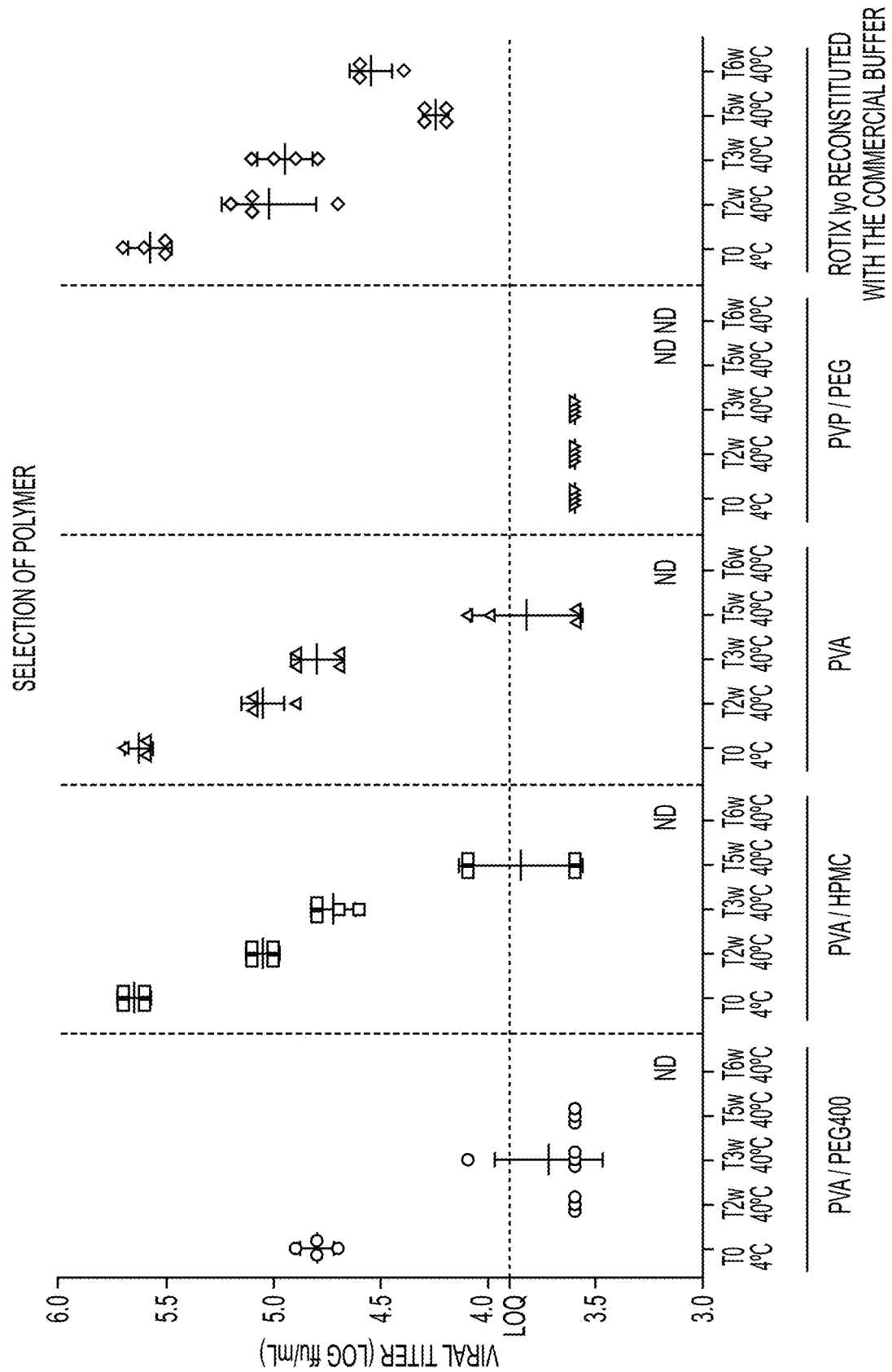
FIG. 7—Impact of polymers on thermostability. Viral titer ($Log_{10}$ ffu/mL, mean and standard deviation) at time points T0 4° C., T2 weeks 40° C., T3 weeks 40° C., T5 weeks 40° C. and T6 weeks 40° C. From left to right, formulations P #94 (90% PVA/10% PEG400), P #95 (90% PVA/10% HPMC), P #97 (100% PVA), P #99 (80% PVP/20% PEG) and Rotarix lyo.

The thermostability of each OTF batch was assessed by determining the viral titer at time points T0 4° C., T2 weeks 40° C., T3 weeks 40° C., T5 weeks 40° C. and T6 weeks 40° C. as described in Example 1(4) above. Four samples were tested at each timepoint. Rotarix lyo (commercial vaccine) was also tested as a control. The results are presented in FIG. 7.

Example 8—Thermostability of Rotavirus OTF Formulations Form 1 to Form 8

Twenty-four Rotavirus OTF batches (P #111-P #134) based on eight different formulations (Form 1 to Form 8) were tested in 3 rounds. OTF batches P #111-P #134 were prepared as described in Example 1(1). The drying time was 90 minutes for all batches. The excipient composition (on a CaCO3-free basis) of each dried OTF formulation is presented in Table 3. Prior to combining with the CaCO3 and PVA stock solution (25% PVA w/v), each excipient stock solution comprised 41.6 mM citric acid, 4 mM $ZnCl_2$, 20% (w/v) trehalose dihydrate or sucrose, 50 mM histidine or phosphate buffer ($K_2HPO_4$), and optionally 25 mM of either arginine, proline, or glycine or 0.4% (w/v) Travasol (on a solid content basis).

The final pH of each wet blend solution was adjusted to 7 for all batches with the exception of batches P #118, P #120 and P #131 (Form 8) for which the pH was adjusted to 7.5. The drying time was set to 90 minutes for all batches.

Once dried, each OTF batch comprised about 59% (w/w) of CaCO₃ and about 41% (w/w) of combined excipient/polymer (PVA) mix. For each OTF batch, the amount excipients mix is presented in table 3.

TABLE 3 excipient composition of dried OTF formulation batches P#111 to P#134

| | OTF batch | | | | | | | |
|---|---|---|---|---|---|---|---|---|
| | P#111, P#123, P#134 (Form1) | P#112, P#121, P#128 (Form2) | P#113, P#125, P#130 (Form3) | P#114, P#119, P#133 (Form4) | P#115, P#126, P#129 (Form5) | P#116, P#124, P#132 (Form6) | P#117, P#122, P#127 (Form7) | P#118, P#120, P#131 (Form8) |
| | % wt w/o CaCO₃ | | | | | | | |
| PVA (Mowiol 8-88) | 53.53 | 53.42 | 52.92 | 53.09 | 52.96 | 53.20 | 53.42 | 53.53 |
| Sucrose | 42.82 | 0.00 | 42.34 | 42.47 | 42.37 | 42.56 | 42.73 | 42.82 |
| Trehalose dihydrate | 0.00 | 42.73 | 0.00 | 0.00 | 0.00 | 0.00 | 0.00 | 0.00 |
| Citric Acid | 1.87 | 1.87 | 1.85 | 1.86 | 1.85 | 1.86 | 1.87 | 1.87 |
| $K_2HPO_4$ | 0.00 | 1.86 | 1.84 | 1.85 | 1.85 | 1.85 | 1.86 | 0.00 |
| $ZnCl_2$ | 0.12 | 0.12 | 0.12 | 0.12 | 0.12 | 0.12 | 0.12 | 0.12 |
| Histidine base | 1.66 | 0.00 | 0.00 | 0.00 | 0.00 | 0.00 | 0.00 | 1.66 |
| Arginine | 0.00 | 0.00 | 0.92 | 0.00 | 0.00 | 0.00 | 0.00 | 0.00 |
| Glycine | 0.00 | 0.00 | 0.00 | 0.00 | 0.00 | 0.40 | 0.00 | 0.00 |
| Proline | 0.00 | 0.00 | 0.00 | 0.61 | 0.00 | 0.00 | 0.00 | 0.00 |
| Travasol | 0.00 | 0.00 | 0.00 | 0.00 | 0.85 | 0.00 | 0.00 | 0.00 |
| Excipient blend pH | 7.0 | 7.0 | 7.0 | 7.0 | 7.0 | 7.0 | 7.0 | 7.5 |

Batches P #111 to P #118 were tested in the first round. Batches P #119 to P #126 were tested in the second round. Batches P #127 to P #134 were tested in the third round.

The Moisture content (residual humidity) of each OTF batch was determined as described in Example 1(3) on a whole content and on a $CaCO_3$-free basis. The Dissolution time of each OTF batch was determined as described in Example 1(5). The thickness of each OTF batch was also measured. The moisture content (MC), thickness and dissolution time of OTF batches P #111 to P #134 are presented in Table 4

TABLE 4 moisture content (MC), thickness and dissolutiotimen of OTF batches P#111 to P#134

| OTF | Round | MC (%) | ±sd | $CaCO_3$-free MC (%) | Thickness (μm) | Dissolution time (sec) | ±sd |
|---|---|---|---|---|---|---|---|
| P#111 | Round1 | 2.20 | 0.14 | 5.34 | 213 | 49.0 | 1.4 |
| P#112 | Round1 | 1.37 | 1.11 | 3.32 | 218 | 48.0 | 1.4 |
| P#113 | Round1 | 2.37 | 0.07 | 5.71 | 209 | 46.0 | 1.4 |
| P#114 | Round1 | 2.20 | 0.15 | 5.31 | 226 | 48.5 | 2.1 |
| P#115 | Round1 | 2.21 | 0.13 | 5.33 | 218 | 49.5 | 3.5 |
| P#116 | Round1 | 2.01 | 0.15 | 5.32 | 215 | 47.5 | 0.7 |
| P#117 | Round1 | 2.13 | 0.00 | 5.33 | 208 | 51.0 | 1.4 |
| P#118 | Round1 | 2.48 | 0.05 | 5.34 | 198 | 47.5 | 2.1 |
| P#119 | Round2 | 2.23 | 0.22 | 5.39 | 214 | 51.0 | 1.4 |
| P#120 | Round2 | 2.46 | 0.32 | 5.92 | 203 | 52.0 | 1.4 |
| P#121 | Round2 | 1.44 | 0.03 | 3.49 | 207 | 48.0 | 1.4 |
| P#122 | Round2 | 2.48 | 0.03 | 5.92 | 210 | 48.5 | 2.1 |
| P#123 | Round2 | 2.44 | 0.03 | 5.92 | 213 | 49.0 | 1.4 |
| P#124 | Round2 | 2.22 | 0.09 | 5.90 | 208 | 47.5 | 0.7 |
| P#125 | Round2 | 1.98 | 0.12 | 4.77 | 214 | 49.0 | 1.4 |
| P#126 | Round2 | 2.48 | 0.00 | 5.98 | 206 | 44.5 | 7.1 |
| P#127 | Round3 | 2.41 | 0.06 | 6.01 | 219 | 48.0 | 2.8 |
| P#128 | Round3 | 1.23 | 0.13 | 2.98 | 213 | 48.0 | 1.4 |
| P#129 | Round3 | 2.26 | 0.08 | 5.45 | 213 | 49.0 | 1.4 |
| P#130 | Round3 | 2.27 | 0.10 | 5.47 | 216 | 51.5 | 2.1 |
| P#131 | Round3 | 2.48 | 0.25 | 6.02 | 212 | 49.0 | 4.2 |
| P#132 | Round3 | 2.24 | 0.06 | 6.0 | 210 | 50.0 | 1.4 |
| P#133 | Round3 | 2.04 | 0.01 | 4.93 | 214 | 46.5 | 5.0 |
| P#134 | Round3 | 2.48 | 0.10 | 6.02 | 195 | 48.0 | 1.4 |

Figure 8:
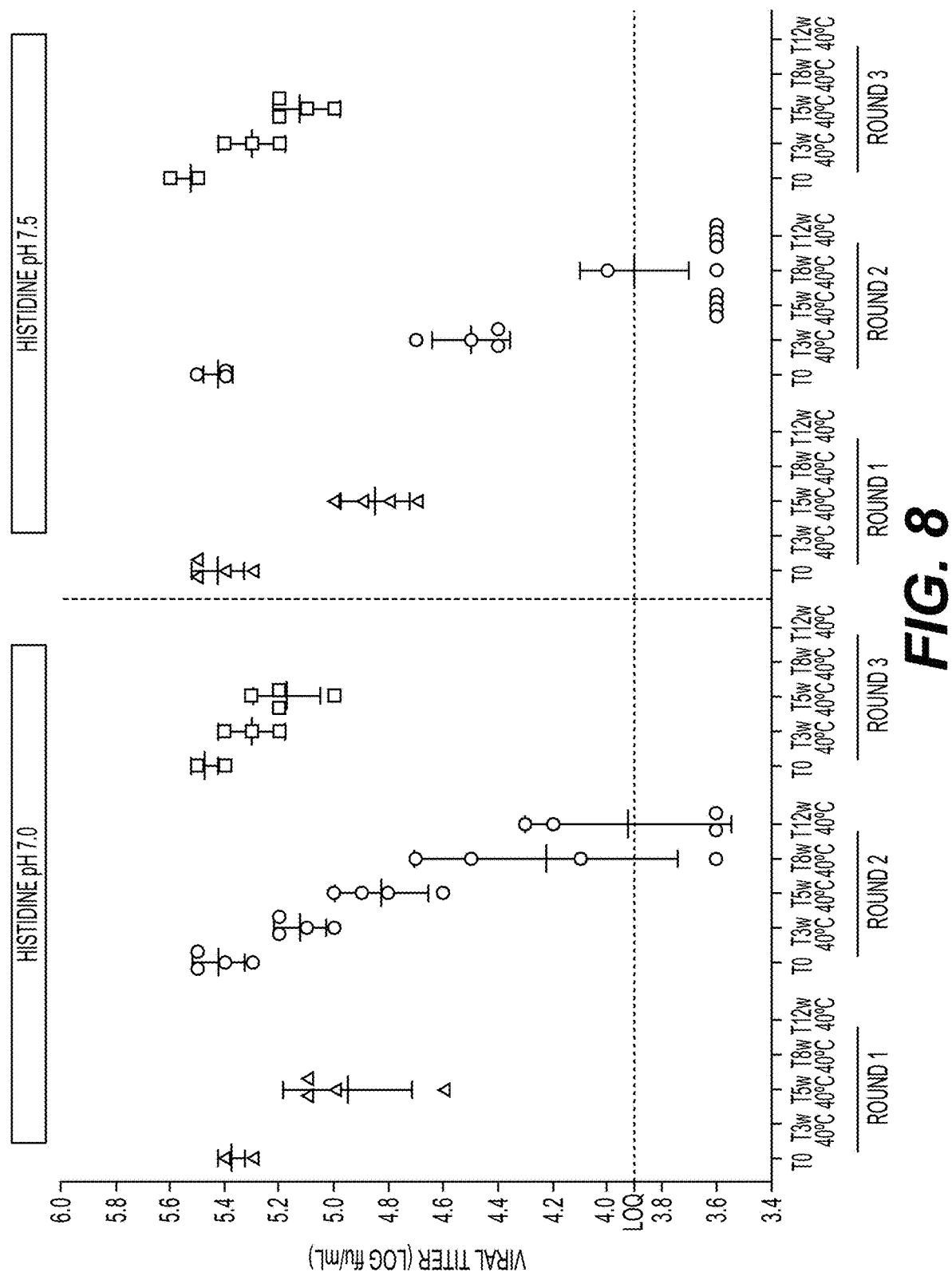
FIG. 8—Thermostability of Form 1 (Histidine pH 7.0) and Form 8 (Histidine pH 7.5). Viral titer ($Log_{10}$ ffu/mL, mean and standard deviation) at time points T0 4° C., T3 weeks 40° C., T5 weeks 40° C., T8 weeks 40° C. and T12 weeks 40° C. for Rounds 1, 2 and 3.
Figure 9:
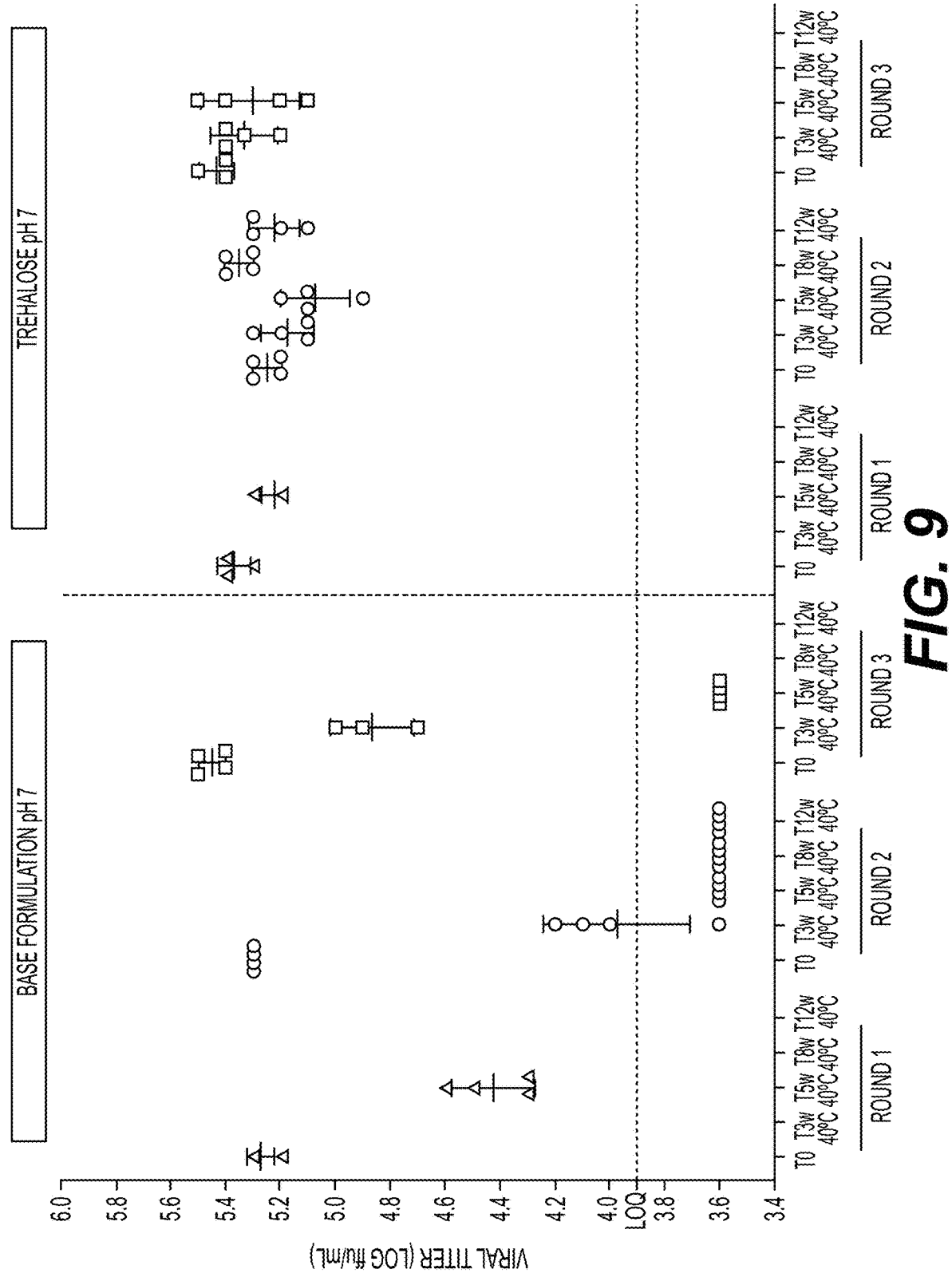
FIG. 9—Thermostability of Form 7 (Base formulation pH 7) and Form 2 (Trehalose pH 7). Viral titer ($Log_{10}$ ffu/mL, mean and standard deviation) at time points T0 4° C., T3 weeks 40° C., T5 weeks 40° C., T8 weeks 40° C. and T12 weeks 40° C. for Rounds 1, 2 and 3.
Figure 10:
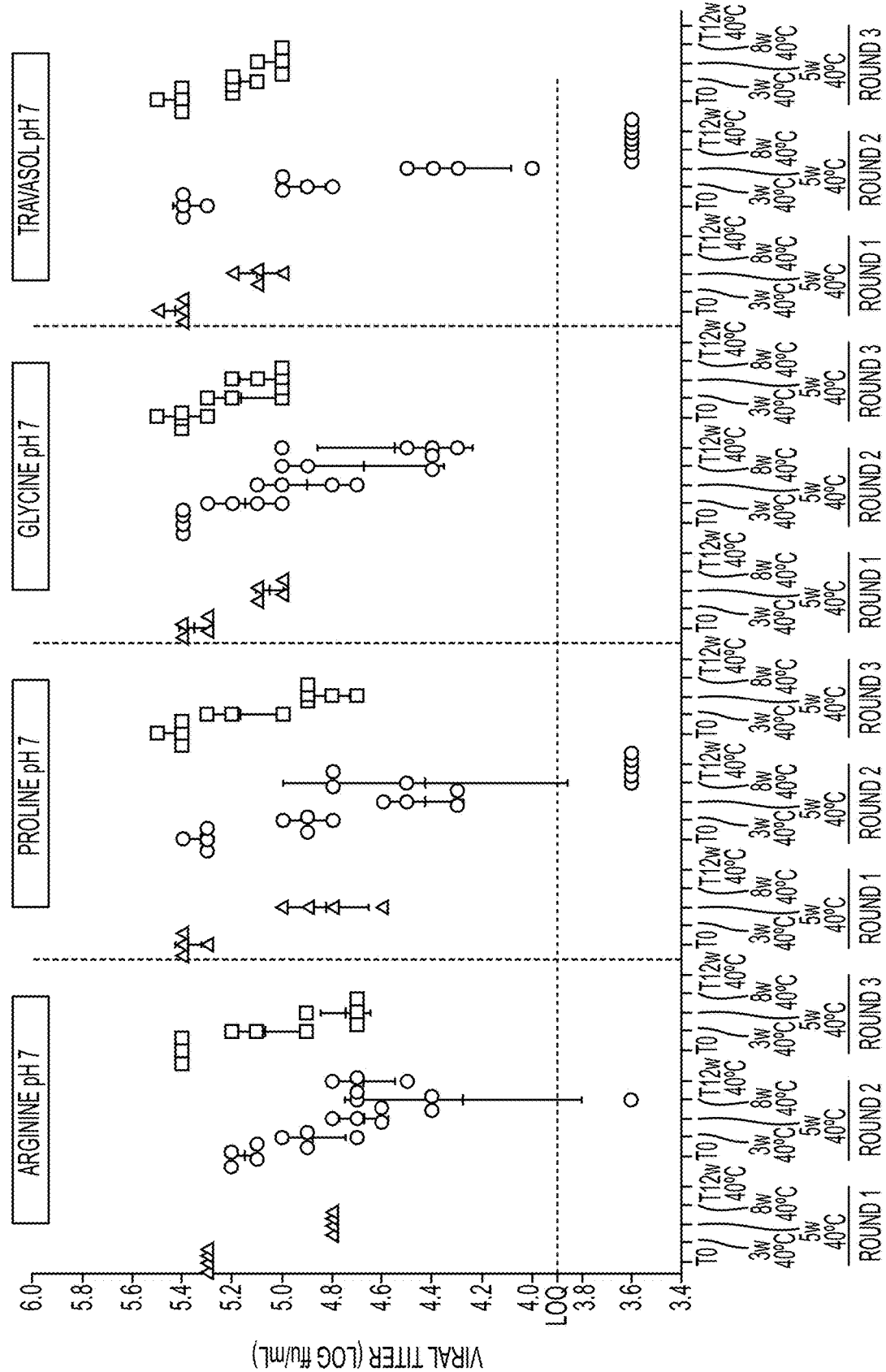
FIG. 10—Thermostability of Form 3 (Arginine pH 7), Form 4 (Proline pH 7), Form 6 (Glycine pH 7) and Form 5 (Travasol pH 7). Viral titer ($Log_{10}$ ffu/mL, mean and standard deviation) at time points T0 4° C., T3 weeks 40° C., T5 weeks 40° C., T8 weeks 40° C. and T12 weeks 40° C. for Rounds 1, 2 and 3.
Figure 11:
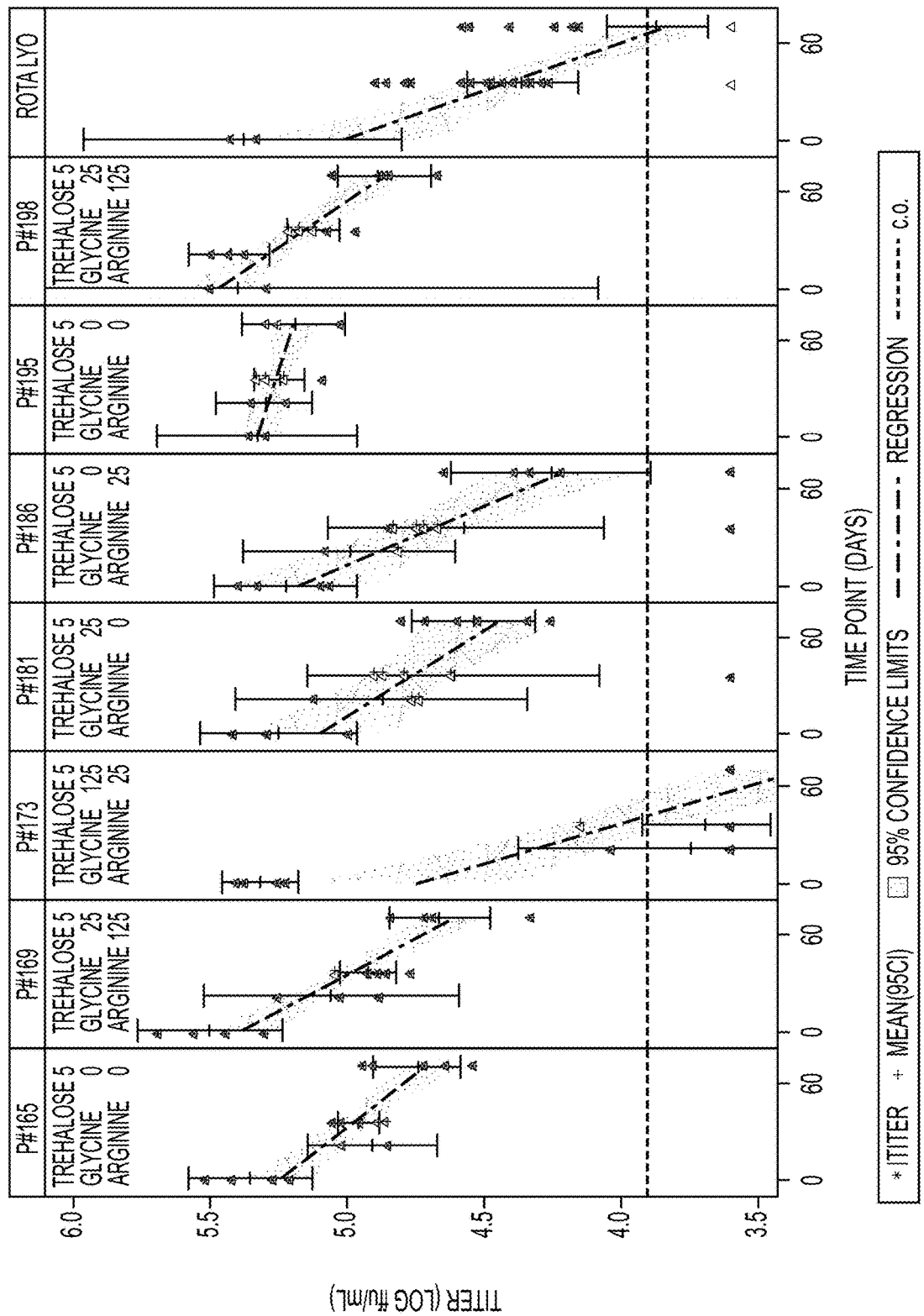
FIG. 11—Thermostability of OTF batches P #165, P #169, P #173, P #181, P #186, P #195, P #198 and Rotarix lyo. Viral titer ($Log_{10}$ ffu/mL, mean and 95% confidence limits) at time points T0 4° C., T3 weeks 40° C., T5 weeks 40° C. and T10 weeks 40° C.
Figure 12:
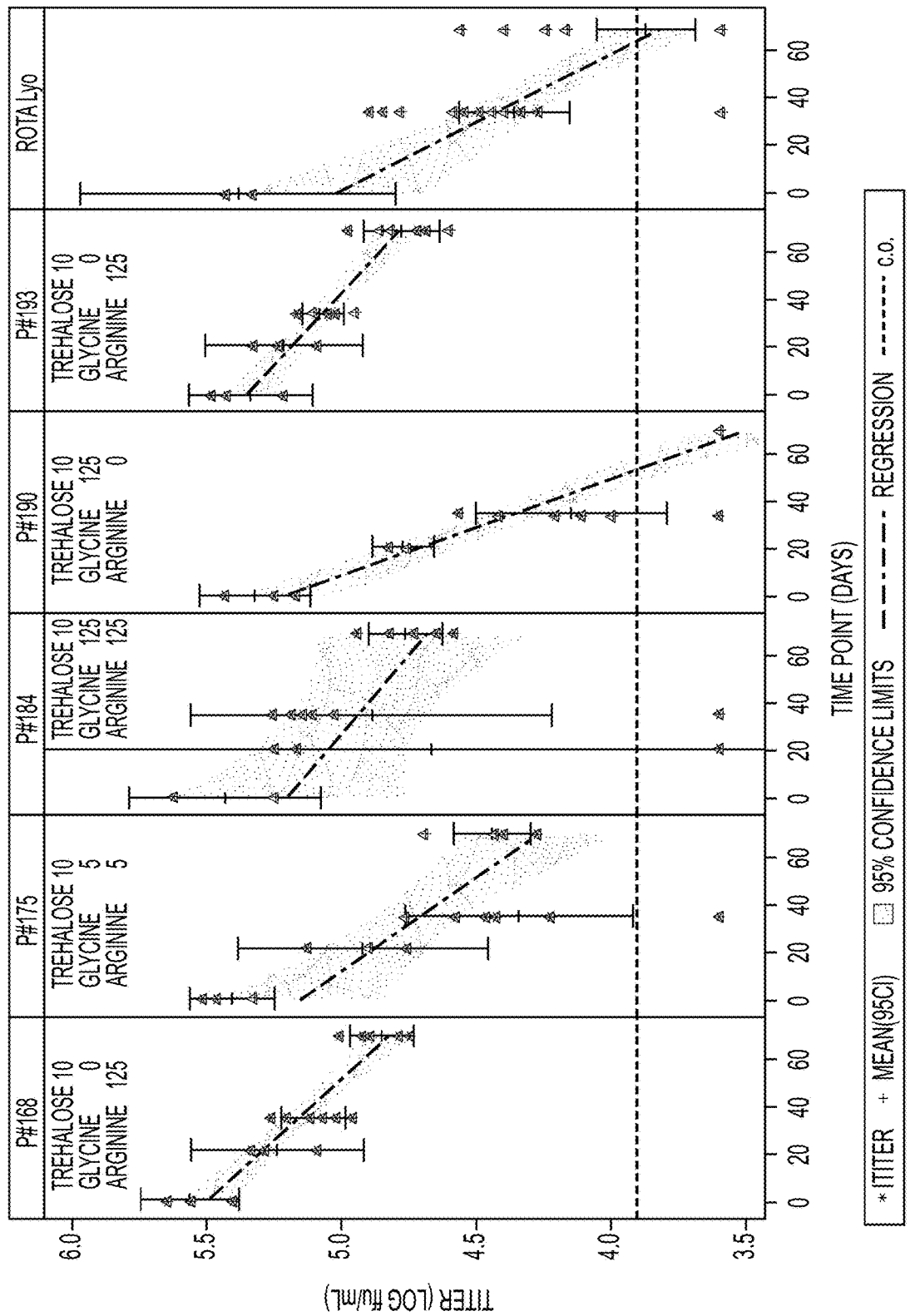
FIG. 12—Thermostability of OTF batches P #168, P #175, P #184, P #190, P #193 and Rotarix lyo. Viral titer ($Log_{10}$ ffu/mL, mean and 95% confidence limits) at time points T0 4° C., T3 weeks 40° C., T5 weeks 40° C. and T10 weeks 40° C.
Figure 13:
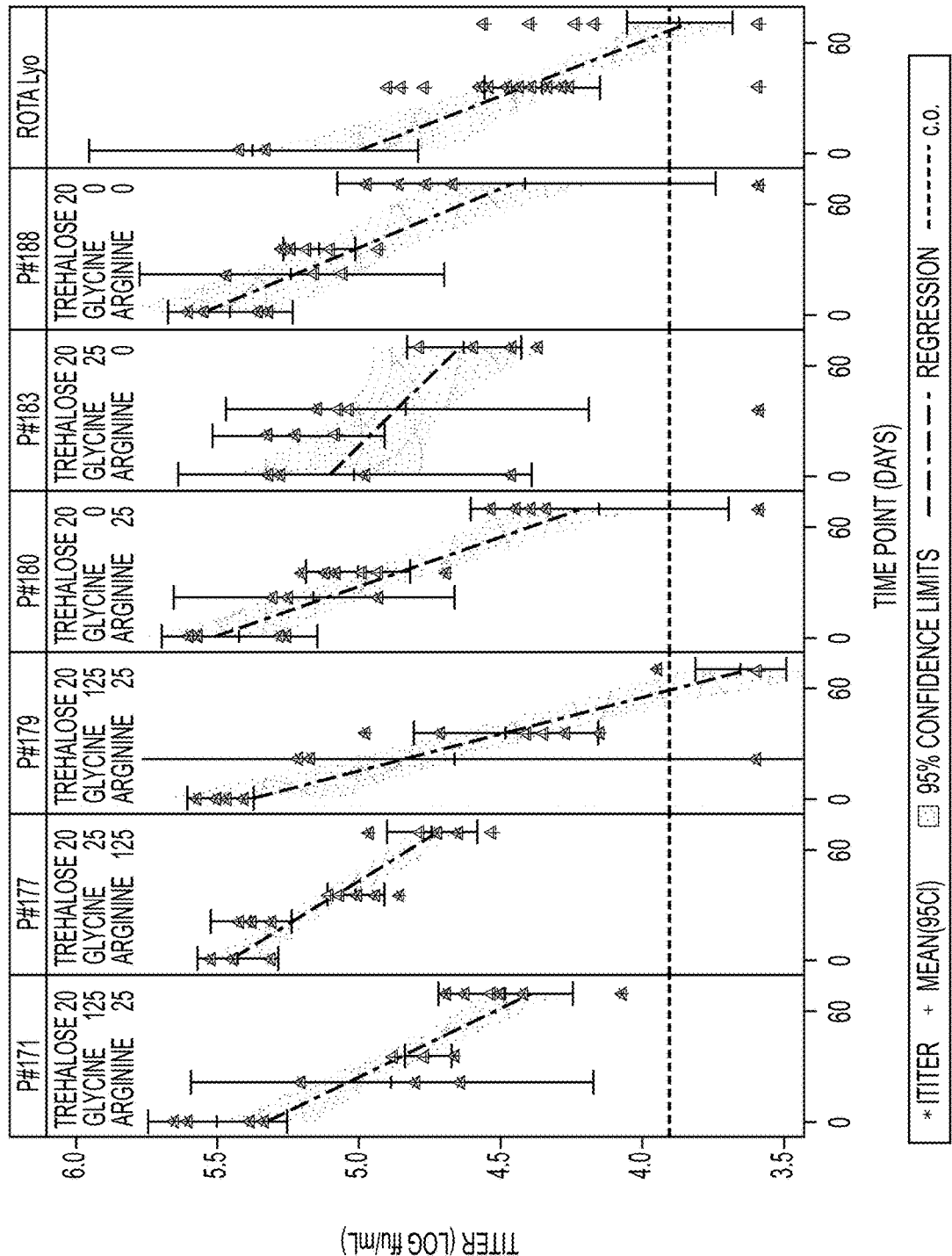
FIG. 13—Thermostability of OTF batches P #171, P #177, P #179, P #180, P #183, P #188 and Rotarix lyo. Viral titer ($Log_{10}$ ffu/mL, mean and 95% confidence limits) at time points T0 4° C., T3 weeks 40° C., T5 weeks 40° C. and T10 weeks 40° C.
Figure 14:
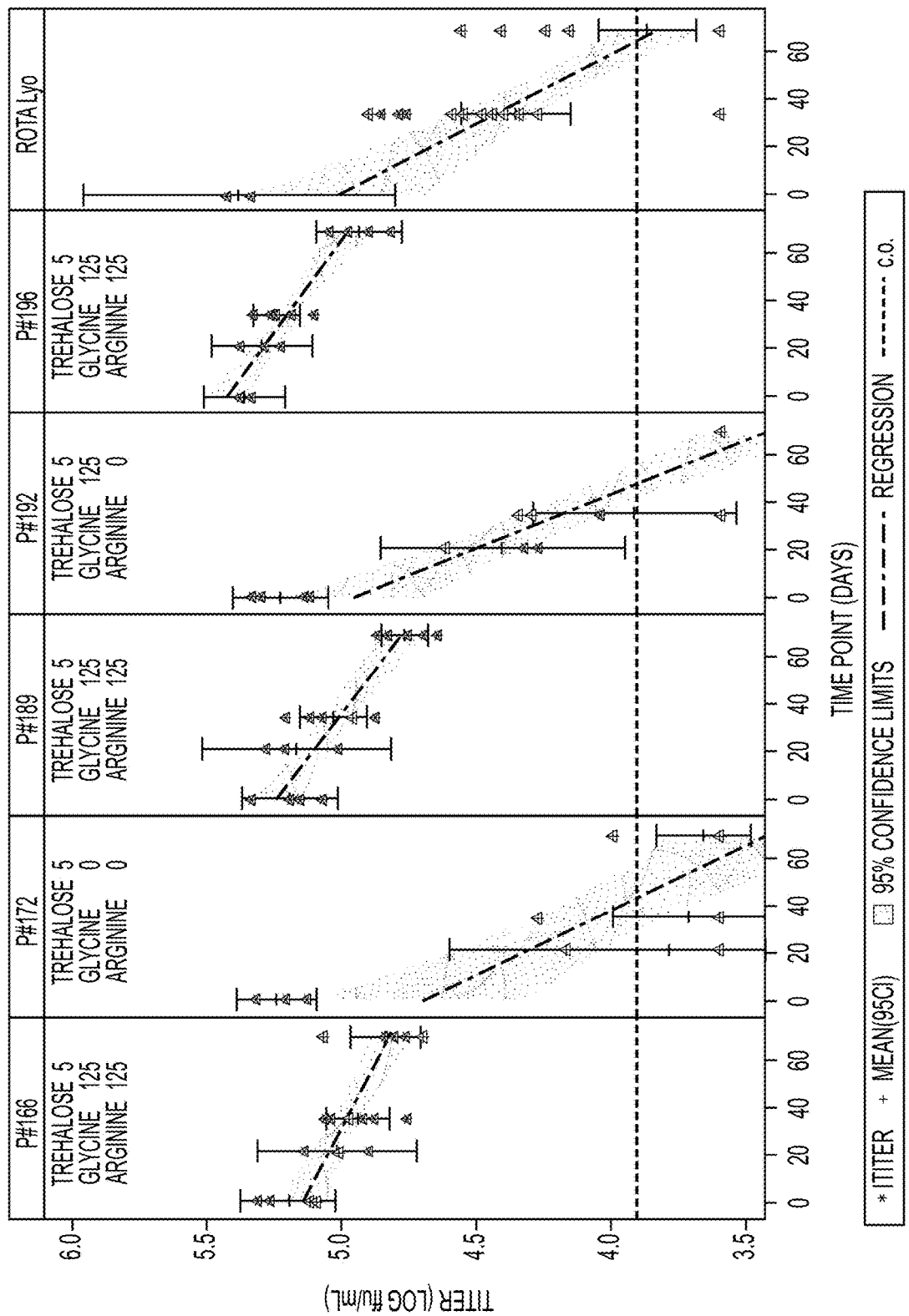
FIG. 14—Thermostability of OTF batches P #166, P #172, P #189, P #192, P #196 and Rotarix lyo. Viral titer ($Log_{10}$ ffu/mL, mean and 95% confidence limits) at time points T0 4° C., T3 weeks 40° C., T5 weeks 40° C. and T10 weeks 40° C.
Figure 15:
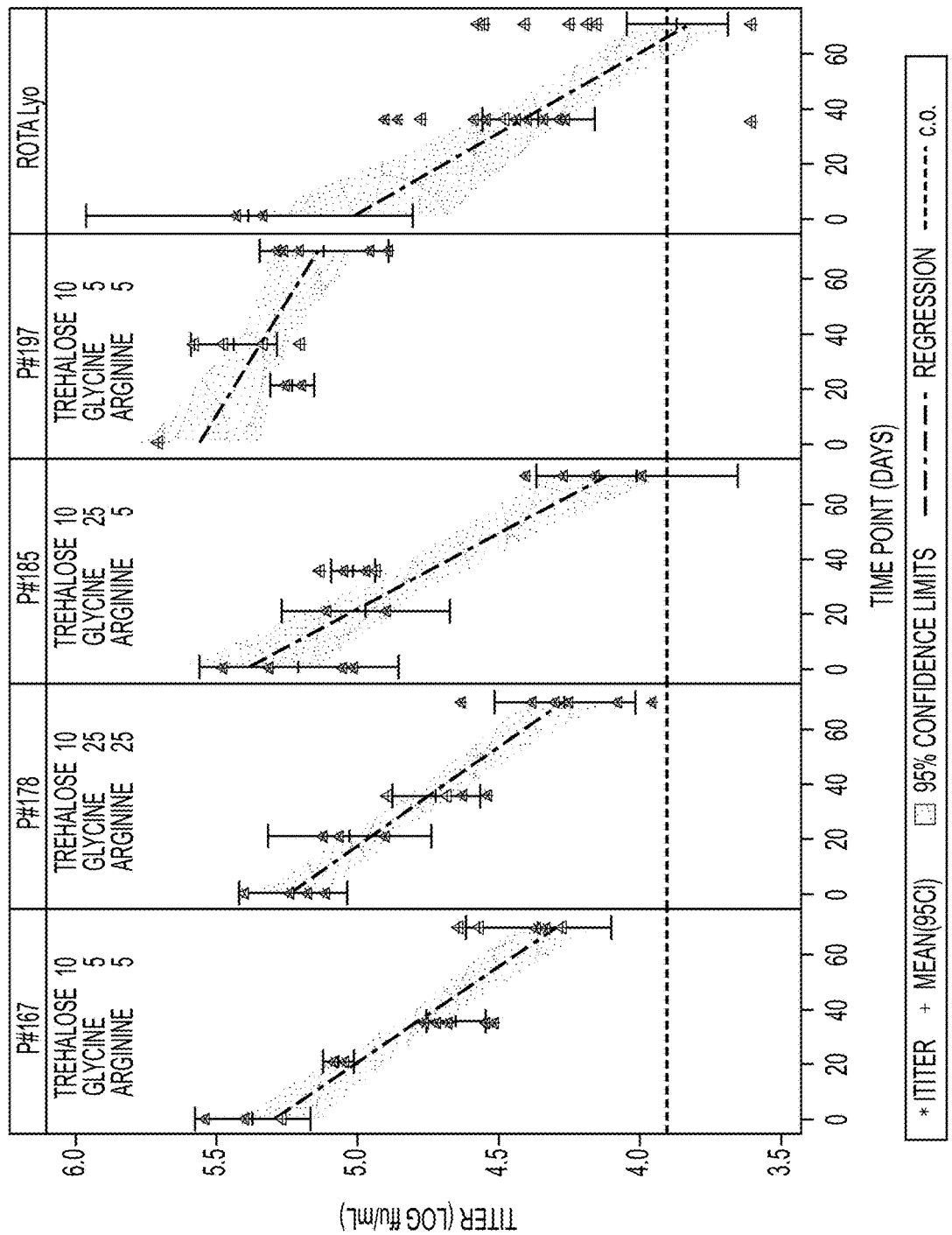
FIG. 15—Thermostability of OTF batches P #167, P #178, P #185, P #197 and Rotarix lyo. Viral titer ($Log_{10}$ ffu/mL, mean and 95% confidence limits) at time points T0 4° C., T3 weeks 40° C., T5 weeks 40° C. and T10 weeks 40° C.
Figure 16:
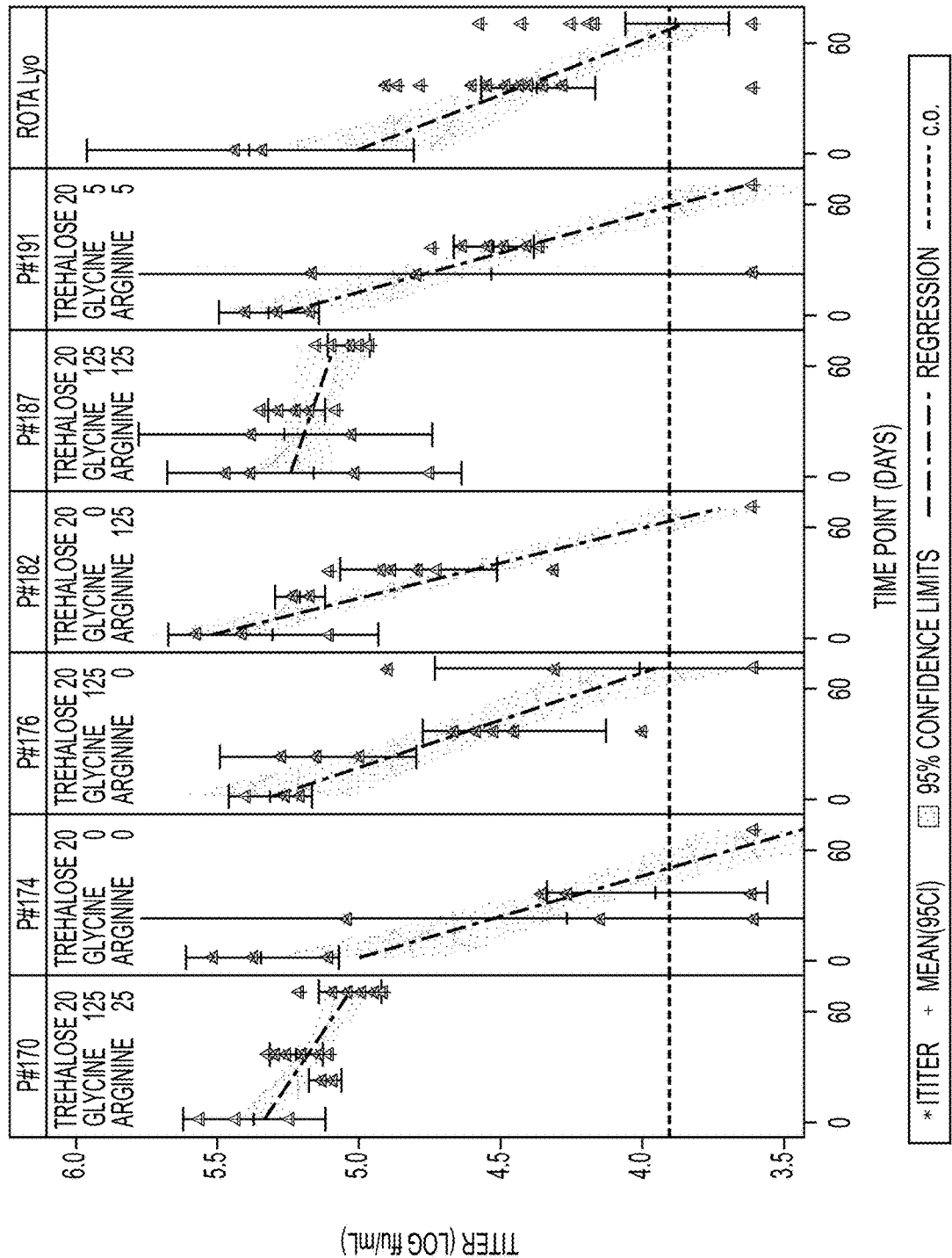
FIG. 16—Thermostability of OTF batches P #170, P #174, P #176, P #182, P #187, P #191 and Rotarix lyo. Viral titer ($Log_{10}$ ffu/mL, mean and 95% confidence limits) at time points T0 4° C., T3 weeks 40° C., T5 weeks 40° C. and T10 weeks 40° C.

The thermostability, of each OTF batch was assessed by determining the viral titer at time points T0 4° C., T3 weeks 40° C., T5 weeks 40° C., T8 weeks 40° C. and T12 weeks 40° C. as described in Example 1(4) above. For each batch, 4 OTFs were tested at each time point. The results for rounds 1, 2 and 3 are presented in FIG. 8 (Form 1, Form 8), FIG. 9 (Form 7, Form 2) and FIG. 10 (Form 3, Form 4, Form 6, Form 5).

Example 9—Thermostability of Rotavirus OTF Formulations P #165 to P #198

Rotavirus OTF batches P #165 to P #198 were prepared as described in Example 1(1). Prior to combining with the CaCO3 and PVA stock solution (25% PVA w/v), each excipient stock solution comprised 41.6 mM citric acid, 4 mM $ZnCl_2$, trehalose dihydrate at a concentration of 5, 10 or 20% (w/v), 50 mM histidine or phosphate buffer ($K_2HPO_4$), and optionally glycine and/or arginine at a concentration of 5, 25 or 125 mM.

The final pH of each wet blend solution was adjusted to 7. The drying time was set to 55 minutes for all batches except for batches P #165 to P #168 for which it was set to 60 minutes, and batches P #170 and P #171 for which it was set to 70 minutes. Once dried, each OTF batch comprised about 50-77% (w/w) of $CaCO_3$ and about 23-50% (w/w) of excipient/polymer (PVA) mix. For each OTF batch, the dry film composition on a $CaCO_3$-free basis consisted of PVA (40-78 wt %), Trehalose dihydrate, $ZnCl_2$ (0.12-0.17 wt %), citric acid (1.8-2.7 wt %), a buffer selected from $K_2PO_4$ (0-2.7 wt %) and histidine base (0-2.4 wt %), and optionally glycine and/or arginine.

OTF batch P #194, used as a benchmark gelatin-containing formulation, had an excipient composition (on $CaCO_3$-free basis) consisting of 49.3 wt % sucrose, 9.9 wt % gelatin, 4.0 wt % sorbitol, 0.15 wt % $CaCl_2$, in addition to 2.0 wt % citric acid, 2.2 wt % $K_2PO_4$, 0.15 wt % $CaCl_2$, 0.14 wt % $ZnCl_2$, and 40.6 wt % PVA. The $CaCO_3$ powder used for this benchmark had an average particle size of 12 micron and the $CaCO_3$ concentration in the wet blend was 20.41% (w/v). The final pH of the wet blend solution was adjusted to 7.15. This benchmark batch was dried at 180 minutes at 60° C.

The choice of buffer, as well as the trehalose, glycine and arginine content of each OTF batch is presented in Table 5.

TABLE 5

Choice of buffer, trehalose, glycine and arginine content in excipient stock solution and dry OTF, and drying time for batches P#165 to P#198

| Form | Buffer | Trehalose (% w/v) Excipient stock solution | Gly (mM) | Arg (mM) | Trehalose | Gly | Arg | Drying time (min) |
|---|---|---|---|---|---|---|---|---|
| | | | | | wt % in OTF on $CaCO_3$-free basis | | | |
| P#165 | Histidine | 5 | 0 | 0 | 15.77 | 0.00 | 0.00 | 60 |
| P#166 | $KPO_4$ | 5 | 125 | 125 | 14.32 | 2.69 | 6.24 | 60 |
| P#167 | $KPO_4$ | 10 | 5 | 5 | 27.08 | 0.10 | 0.24 | 60 |
| P#168 | Histidine | 10 | 0 | 125 | 25.72 | 0.00 | 5.60 | 60 |
| P#169 | Histidine | 5 | 25 | 125 | 14.67 | 0.55 | 6.39 | 55 |
| P#170 | $KPO_4$ | 20 | 125 | 25 | 41.52 | 1.95 | 0.91 | 70 |
| P#171 | Histidine | 20 | 125 | 25 | 41.60 | 1.95 | 0.91 | 70 |
| P#172 | $KPO_4$ | 5 | 0 | 0 | 15.72 | 0.00 | 0.00 | 55 |
| P#173 | Histidine | 5 | 125 | 25 | 15.11 | 2.84 | 1.32 | 55 |
| P#174 | $KPO_4$ | 20 | 0 | 0 | 42.73 | 0.00 | 0.00 | 55 |
| P#175 | Histidine | 10 | 5 | 5 | 27.15 | 0.10 | 0.24 | 55 |
| P#176 | $KPO_4$ | 20 | 125 | 0 | 41.22 | 1.93 | 0.00 | 55 |
| P#177 | Histidine | 20 | 25 | 125 | 40.76 | 0.38 | 4.44 | 55 |
| P#178 | $KPO_4$ | 10 | 25 | 25 | 26.72 | 0.50 | 1.16 | 55 |
| P#179 | Histidine | 20 | 125 | 25 | 41.60 | 1.95 | 0.91 | 55 |
| P#180 | Histidine | 20 | 0 | 25 | 42.43 | 0.00 | 0.92 | 55 |
| P#181 | Histidine | 5 | 25 | 0 | 15.68 | 0.59 | 0.00 | 55 |
| P#182 | $KPO_4$ | 20 | 0 | 125 | 40.83 | 0.00 | 4.45 | 55 |

TABLE 5-continued

Choice of buffer, trehalose, glycine and arginine content in excipient stock solution and dry OTF, and drying time for batches P#165 to P#198

| Form | Buffer | Trehalose (% w/v) Excipient stock solution | Gly (mM) | Arg (mM) | Trehalose wt % in OTF on CaCO$_3$-free basis | Gly | Arg | Drying time (min) |
|---|---|---|---|---|---|---|---|---|
| P#183 | Histidine | 20 | 25 | 0 | 42.65 | 0.40 | 0.00 | 55 |
| P#184 | Histidine | 10 | 125 | 125 | 25.11 | 2.36 | 5.47 | 55 |
| P#185 | KPO$_4$ | 10 | 25 | 5 | 26.97 | 0.51 | 0.23 | 55 |
| P#186 | Histidine | 5 | 0 | 25 | 15.56 | 0.00 | 1.36 | 55 |
| P#187 | KPO$_4$ | 20 | 125 | 125 | 40.07 | 1.88 | 4.36 | 55 |
| P#188 | Histidine | 20 | 0 | 0 | 42.82 | 0.00 | 0.00 | 55 |
| P#189 | KPO$_4$ | 5 | 125 | 125 | 14.32 | 2.69 | 6.24 | 55 |
| P#190 | Histidine | 10 | 125 | 0 | 26.56 | 2.49 | 0.00 | 55 |
| P#191 | KPO$_4$ | 20 | 5 | 5 | 42.62 | 0.08 | 0.19 | 55 |
| P#192 | KPO$_4$ | 5 | 125 | 0 | 15.27 | 2.87 | 0.00 | 55 |
| P#193 | Histidine | 10 | 0 | 125 | 25.72 | 0.00 | 5.60 | 55 |
| P#194* | Benchmark | 0 | 0 | 0 | 0 | 0 | 0 | 180 |
| P#195 | Histidine | 5 | 0 | 0 | 15.77 | 0.00 | 0.00 | 55 |
| P#196 | KPO$_4$ | 5 | 125 | 125 | 14.32 | 2.69 | 6.24 | 55 |
| P#197 | KPO$_4$ | 10 | 5 | 5 | 27.08 | 0.10 | 0.24 | 55 |
| P#198 | Histidine | 5 | 25 | 125 | 14.67 | 0.55 | 6.39 | 55 |

*P#194 (benchmark) also contained sucrose, gelatin, sorbitol, CaCl$_2$ and was dried at for 3 hours at 60° C.

The Moisture content (residual humidity) of each OTF batch was determined as described in Example 1(3) on a CaCO$_3$-free basis. The Dissolution time of each OTF batch was determined as described in Example 1(5). The thickness of each OTF batch was also measured. The flexibility of each OTF batch was determined as described in Example 1(7).

The moisture content (MC), thickness and dissolution time of OTF batches P #165 to P #198 are presented in table 6.

TABLE 6

Moisture content (MC), dissolution time, thickness and flexibility of OTF batches P #165 to P #198

| OTF Batch | CaCO$_3$-free MC (%) | Dissolution (sec) | Thickness (μm) | Flexbility |
|---|---|---|---|---|
| P #165 | 4.3 | 53.0 | 207 | flex/brit |
| P #166 | 3.7 | 49.0 | 213 | flex/brit |
| P #167 | 4.5 | 47.5 | 215 | flex/brit |
| P #168 | 6.2 | 47.5 | 191 | brit |
| P #169 | 5.7 | 49.0 | 188 | flex/brit |
| P #170 | 4.8 | 47.5 | 216 | brit |
| P #171 | 5.0 | 49.0 | 217 | brit |
| P #172 | 5.3 | 51.5 | 200 | flex |
| P #173 | 5.6 | 50.0 | 186 | flex |
| P #174 | 7.4 | 47.5 | 218 | flex |
| P #175 | 6.0 | 51.0 | 192 | flex |
| P #176 | 7.0 | 51.5 | 206 | flex |
| P #177 | 6.9 | 48.0 | 193 | flex |
| P #178 | 4.8 | 50.5 | 212 | flex |
| P #179 | 7.1 | 49.5 | 200 | flex |
| P #180 | 7.0 | 51.0 | 195 | flex |
| P #181 | 3.2 | 48.5 | 208 | brit |
| P #182 | 6.7 | 51.0 | 206 | flex |
| P #183 | 7.5 | 50.0 | 199 | flex/brit |
| P #184 | 5.9 | 49.5 | 190 | flex/brit |
| P #185 | 3.9 | 49.0 | 198 | flex/brit |
| P #186 | 5.4 | 51.5 | 198 | flex/brit |
| P #187 | 7.6 | 47.5 | 199 | flex |
| P #188 | 7.3 | 47.5 | 206 | flex/brit |
| P #189 | 4.2 | 52.0 | 215 | flex/brit |
| P #190 | 7.6 | 50.0 | 199 | flex |
| P #191 | 5.4 | 50.5 | 201 | flex |
| P #192 | 5.9 | 51.5 | 198 | flex |
| P #193 | 6.2 | 51.0 | 198 | flex |
| P #194 | 4.9 | 94.0 | 264 | brit |
| P #195 | 2.8 | 51.5 | 198 | brit |
| P #196 | 5.1 | 51.5 | 204 | flex/brit |
| P #197 | 3.4 | 50.5 | 203 | flex/brit |
| P #198 | 5.0 | 48.0 | 192 | flex/brit |

The thermostability of each OTF batch was assessed by determining the viral titer at time points T0 4° C. (4 OTFs for P #165-196, 2 for P #194-P #198), T3 weeks 40° C. (3 OTFs), T5 weeks 40° C. (6 OTFs) and T10 weeks 40° C. (6 OTFs) as described in Example 1(4) above. Rotarix lyo (commercial vaccine) was also tested as a control.

The results are presented in Table 7 and Table 8 below and in FIGS. 11 to 16.

TABLE 7

Viral titer of OTF batches P#165 to P#198 over time

| OTF batch | Day | N° of samples | Viral titer (Log$_{10}$ ffu/mL) | | | Mean loss from Day 0 | | |
|---|---|---|---|---|---|---|---|---|
| | | | Mean by time-point | Lower 95% CI | Upper 95% CI | Mean by time-point | Lower 95% CI | Upper 95% CI |
| P#165 | 0 | 4 | 5.36 | 5.14 | 5.58 | | | |
| P#165 | 21 | 3 | 4.91 | 4.68 | 5.15 | 0.45 | 0.25 | 0.65 |
| P#165 | 35 | 6 | 4.96 | 4.89 | 5.04 | 0.40 | 0.23 | 0.56 |
| P#165 | 70 | 6 | 4.75 | 4.59 | 4.91 | 0.61 | 0.45 | 0.78 |
| P#166 | 0 | 4 | 5.20 | 5.03 | 5.37 | | | |
| P#166 | 21 | 3 | 5.02 | 4.73 | 5.31 | 0.18 | −0.01 | 0.37 |
| P#166 | 35 | 6 | 4.94 | 4.82 | 5.06 | 0.26 | 0.10 | 0.42 |
| P#166 | 70 | 6 | 4.84 | 4.71 | 4.97 | 0.36 | 0.20 | 0.52 |
| P#167 | 0 | 4 | 5.37 | 5.17 | 5.58 | | | |
| P#167 | 21 | 3 | 5.07 | 5.02 | 5.12 | 0.30 | 0.04 | 0.57 |
| P#167 | 35 | 6 | 4.65 | 4.55 | 4.75 | 0.72 | 0.50 | 0.95 |
| P#167 | 70 | 6 | 4.36 | 4.10 | 4.62 | 1.01 | 0.79 | 1.24 |
| P#168 | 0 | 4 | 5.57 | 5.38 | 5.75 | | | |
| P#168 | 21 | 3 | 5.24 | 4.92 | 5.56 | 0.33 | 0.14 | 0.51 |
| P#168 | 35 | 6 | 5.11 | 4.99 | 5.23 | 0.46 | 0.30 | 0.62 |
| P#168 | 70 | 6 | 4.86 | 4.74 | 4.97 | 0.71 | 0.56 | 0.87 |
| P#169 | 0 | 4 | 5.51 | 5.24 | 5.77 | | | |

TABLE 7-continued

Viral titer of OTF batches P#165 to P#198 over time

| OTF batch | Day | N° of samples | Viral titer (Log$_{10}$ ffu/mL) Mean by time-point | Lower 95% CI | Upper 95% CI | Mean loss from Day 0 Mean by time-point | Lower 95% CI | Upper 95% CI |
|---|---|---|---|---|---|---|---|---|
| P#169 | 21 | 3 | 5.06 | 4.59 | 5.53 | 0.45 | 0.20 | 0.69 |
| P#169 | 35 | 6 | 4.93 | 4.82 | 5.03 | 0.58 | 0.37 | 0.79 |
| P#169 | 70 | 6 | 4.67 | 4.48 | 4.85 | 0.84 | 0.63 | 1.05 |
| P#170 | 0 | 4 | 5.37 | 5.12 | 5.62 | | | |
| P#170 | 21 | 3 | 5.12 | 5.06 | 5.17 | 0.25 | 0.07 | 0.42 |
| P#170 | 35 | 6 | 5.22 | 5.13 | 5.32 | 0.15 | 0.00 | 0.29 |
| P#170 | 70 | 6 | 5.03 | 4.92 | 5.14 | 0.34 | 0.19 | 0.48 |
| P#171 | 0 | 4 | 5.51 | 5.25 | 5.76 | | | |
| P#171 | 21 | 3 | 4.89 | 4.18 | 5.61 | 0.61 | 0.31 | 0.91 |
| P#171 | 35 | 6 | 4.76 | 4.67 | 4.84 | 0.75 | 0.49 | 1.00 |
| P#171 | 70 | 6 | 4.48 | 4.25 | 4.71 | 1.02 | 0.77 | 1.28 |
| P#172 | 0 | 4 | 5.24 | 5.10 | 5.39 | | | |
| P#172 | 21 | 3 | 3.79 | 2.97 | 4.61 | 1.46 | 1.09 | 1.82 |
| P#172 | 35 | 6 | 3.71 | 3.42 | 4.00 | 1.53 | 1.22 | 1.84 |
| P#172 | 70 | 6 | 3.67 | 3.50 | 3.84 | 1.58 | 1.27 | 1.89 |
| P#173 | 0 | 4 | 5.32 | 5.18 | 5.46 | | | |
| P#173 | 21 | 3 | 3.75 | 3.11 | 4.38 | 1.58 | 1.31 | 1.84 |
| P#173 | 35 | 6 | 3.69 | 3.46 | 3.92 | 1.63 | 1.41 | 1.86 |
| P#173 | 70 | 6 | 3.60 | | | 1.72 | 1.50 | 1.95 |
| P#174 | 0 | 4 | 5.34 | 5.07 | 5.61 | | | |
| P#174 | 21 | 3 | 4.26 | 2.46 | 6.07 | 1.08 | 0.51 | 1.65 |
| P#174 | 35 | 6 | 3.94 | 3.55 | 4.34 | 1.40 | 0.91 | 1.88 |
| P#174 | 70 | 6 | 3.60 | | | 1.74 | 1.26 | 2.22 |
| P#175 | 0 | 4 | 5.41 | 5.26 | 5.57 | | | |
| P#175 | 21 | 3 | 4.93 | 4.47 | 5.39 | 0.48 | 0.06 | 0.91 |
| P#175 | 35 | 6 | 4.35 | 3.92 | 4.77 | 1.07 | 0.71 | 1.42 |
| P#175 | 70 | 6 | 4.44 | 4.30 | 4.59 | 0.97 | 0.61 | 1.33 |
| P#176 | 0 | 4 | 5.31 | 5.17 | 5.46 | | | |
| P#176 | 21 | 3 | 5.14 | 4.79 | 5.48 | 0.18 | −0.42 | 0.78 |
| P#176 | 35 | 5 | 4.44 | 4.12 | 4.76 | 0.87 | 0.34 | 1.40 |
| P#176 | 70 | 5 | 4.00 | 3.27 | 4.73 | 1.31 | 0.79 | 1.84 |
| P#177 | 0 | 4 | 5.43 | 5.29 | 5.58 | | | |
| P#177 | 21 | 3 | 5.38 | 5.24 | 5.57 | 0.05 | −0.13 | 0.23 |
| P#177 | 35 | 6 | 5.02 | 4.92 | 5.12 | 0.42 | 0.26 | 0.57 |
| P#177 | 70 | 6 | 4.75 | 4.59 | 4.90 | 0.69 | 0.53 | 0.84 |
| P#178 | 0 | 4 | 5.24 | 5.04 | 5.43 | | | |
| P#178 | 21 | 3 | 5.03 | 4.74 | 5.32 | 0.21 | −0.08 | 0.49 |
| P#178 | 35 | 6 | 4.72 | 4.57 | 4.87 | 0.51 | 0.27 | 0.76 |
| P#178 | 70 | 6 | 4.27 | 4.02 | 4.52 | 0.97 | 0.73 | 1.21 |
| P#180 | 0 | 4 | 5.43 | 5.15 | 5.71 | | | |
| P#180 | 21 | 3 | 5.17 | 4.67 | 5.67 | 0.26 | −0.22 | 0.74 |
| P#180 | 35 | 6 | 5.01 | 4.82 | 5.20 | 0.42 | 0.02 | 0.82 |
| P#180 | 70 | 6 | 4.16 | 3.70 | 4.62 | 1.27 | 0.87 | 1.68 |
| P#181 | 0 | 4 | 5.25 | 4.97 | 5.54 | | | |
| P#181 | 21 | 3 | 4.88 | 4.34 | 5.41 | 0.37 | −0.17 | 0.92 |
| P#181 | 35 | 6 | 4.61 | 4.08 | 5.15 | 0.64 | 0.18 | 1.10 |
| P#181 | 70 | 6 | 4.54 | 4.32 | 4.77 | 0.71 | 0.25 | 1.17 |
| P#182 | 0 | 4 | 5.30 | 4.93 | 5.67 | | | |
| P#182 | 21 | 3 | 5.21 | 5.12 | 5.30 | 0.09 | −0.21 | 0.39 |
| P#182 | 35 | 6 | 4.79 | 4.51 | 5.06 | 0.51 | 0.26 | 0.76 |
| P#182 | 70 | 6 | 3.60 | | | 1.70 | 1.44 | 1.95 |
| P#183 | 0 | 4 | 5.02 | 4.40 | 5.64 | | | |
| P#183 | 21 | 3 | 5.22 | 4.92 | 5.52 | −0.20 | −0.87 | 0.46 |
| P#183 | 35 | 6 | 4.83 | 4.20 | 5.47 | 0.19 | −0.37 | 0.75 |
| P#183 | 70 | 6 | 4.64 | 4.45 | 4.83 | 0.38 | −0.18 | 0.94 |
| P#184 | 0 | 4 | 5.43 | 5.08 | 5.79 | | | |
| P#184 | 21 | 3 | 4.68 | 2.36 | 6.99 | 0.76 | −0.08 | 1.60 |
| P#184 | 35 | 6 | 4.89 | 4.22 | 5.56 | 0.54 | −0.17 | 1.25 |
| P#184 | 70 | 6 | 4.76 | 4.63 | 4.90 | 0.67 | −0.04 | 1.38 |
| P#185 | 0 | 4 | 5.21 | 4.86 | 5.57 | | | |
| P#185 | 21 | 3 | 4.97 | 4.68 | 5.27 | 0.24 | −0.13 | 0.62 |
| P#185 | 35 | 6 | 5.02 | 4.94 | 5.09 | 0.20 | −0.12 | 0.51 |
| P#185 | 70 | 6 | 4.01 | 3.65 | 4.37 | 1.21 | 0.89 | 1.52 |
| P#186 | 0 | 4 | 5.23 | 4.97 | 5.49 | | | |
| P#186 | 21 | 3 | 5.00 | 4.61 | 5.38 | 0.23 | −0.35 | 0.81 |
| P#186 | 35 | 6 | 4.57 | 4.07 | 5.08 | 0.66 | 0.17 | 1.15 |
| P#186 | 70 | 6 | 4.26 | 3.89 | 4.63 | 0.97 | 0.48 | 1.46 |
| P#188 | 0 | 4 | 5.46 | 5.24 | 5.68 | | | |
| P#188 | 21 | 3 | 5.24 | 4.70 | 5.77 | 0.22 | −0.41 | 0.86 |
| P#188 | 35 | 6 | 5.14 | 5.02 | 5.27 | 0.32 | −0.22 | 0.85 |
| P#188 | 70 | 6 | 4.41 | 3.74 | 5.09 | 1.05 | 0.51 | 1.58 |
| P#189 | 0 | 4 | 5.70 | 5.02 | 5.37 | | | |
| P#189 | 21 | 3 | 5.17 | 4.81 | 5.52 | 0.03 | −0.15 | 0.21 |
| P#189 | 35 | 6 | 5.03 | 4.91 | 5.16 | 0.16 | 0.01 | 0.31 |
| P#189 | 70 | 6 | 4.77 | 4.68 | 4.86 | 0.43 | 0.27 | 0.58 |
| P#190 | 0 | 4 | 5.33 | 5.12 | 5.54 | | | |
| P#190 | 21 | 3 | 4.78 | 4.66 | 4.90 | 0.55 | 0.21 | 0.89 |
| P#190 | 35 | 6 | 4.15 | 3.80 | 4.51 | 1.17 | 0.89 | 1.46 |
| P#190 | 70 | 6 | 3.60 | | | 1.73 | 1.44 | 2.01 |
| P#191 | 0 | 4 | 5.31 | 5.14 | 5.48 | | | |
| P#191 | 21 | 3 | 4.52 | 2.49 | 6.55 | 0.79 | 0.28 | 1.30 |
| P#191 | 35 | 6 | 4.52 | 4.38 | 4.67 | 0.79 | 0.36 | 1.22 |
| P#191 | 70 | 6 | 3.60 | | | 1.71 | 1.28 | 2.14 |
| P#192 | 0 | 4 | 5.23 | 5.05 | 5.40 | | | |
| P#192 | 21 | 3 | 4.41 | 3.95 | 4.86 | 0.82 | 0.46 | 1.19 |
| P#192 | 35 | 6 | 3.91 | 3.54 | 4.29 | 1.31 | 1.01 | 1.62 |
| P#192 | 70 | 6 | 3.60 | | | 1.63 | 1.32 | 1.94 |
| P#179 | 0 | 4 | 5.50 | 5.38 | 5.61 | | | |
| P#179 | 21 | 3 | 4.67 | 2.37 | 6.97 | 0.83 | 0.19 | 1.47 |
| P#179 | 35 | 6 | 4.49 | 4.16 | 4.81 | 1.01 | 0.47 | 1.55 |
| P#179 | 70 | 6 | 3.66 | 3.51 | 3.81 | 1.84 | 1.30 | 2.38 |
| P#187 | 0 | 4 | 5.15 | 4.63 | 5.68 | | | |
| P#187 | 21 | 3 | 5.26 | 4.74 | 5.78 | −0.11 | −0.40 | 0.18 |
| P#187 | 35 | 6 | 5.22 | 5.12 | 5.31 | −0.06 | −0.31 | 0.18 |
| P#187 | 70 | 6 | 5.04 | 4.97 | 5.11 | 0.11 | −0.13 | 0.36 |
| P#193 | 0 | 4 | 5.34 | 5.12 | 5.56 | | | |
| P#193 | 71 | 3 | 5.22 | 4.93 | 5.51 | 0.12 | −0.06 | 0.31 |
| P#193 | 35 | 6 | 5.07 | 4.99 | 5.14 | 0.27 | 0.11 | 0.43 |
| P#193 | 70 | 6 | 4.78 | 4.65 | 4.92 | 0.56 | 0.40 | 0.71 |
| P#195 | 0 | 2 | 5.33 | 4.97 | 2.70 | | | |
| P#195 | 21 | 3 | 5.31 | 5.13 | 5.49 | 0.02 | −0.16 | 0.21 |
| P#195 | 35 | 6 | 5.25 | 5.16 | 5.34 | 0.08 | −0.09 | 0.24 |
| P#195 | 70 | 4 | 5.20 | 5.01 | 5.39 | 0.13 | −0.04 | 0.31 |
| P#196 | 0 | 2 | 5.36 | 5.21 | 5.51 | | | |
| P#196 | 21 | 3 | 5.29 | 5.11 | 5.48 | 0.07 | −0.10 | 0.23 |
| P#196 | 35 | 6 | 5.24 | 5.16 | 5.33 | 0.12 | −0.03 | 0.27 |
| P#196 | 70 | 4 | 4.94 | 4.78 | 5.10 | 0.42 | 0.27 | 0.58 |
| P#197 | 0 | 1 | 5.71 | | | | | |
| P#197 | 21 | 3 | 5.24 | 5.16 | 5.31 | 0.47 | 0.10 | 0.85 |
| P#197 | 35 | 6 | 5.44 | 5.29 | 5.60 | 0.27 | −0.08 | 0.62 |
| P#197 | 70 | 5 | 5.13 | 4.90 | 5.35 | 0.58 | 0.23 | 0.94 |
| P#198 | 0 | 2 | 5.40 | 4.09 | 6.77 | | | |
| P#198 | 21 | 3 | 5.44 | 5.29 | 5.59 | −0.04 | −0.25 | 0.18 |
| P#198 | 35 | 6 | 5.13 | 5.03 | 5.72 | 0.28 | 0.08 | 0.47 |
| P#198 | 70 | 5 | 4.87 | 4.70 | 5.04 | 0.54 | 0.33 | 0.74 |
| LYO | 0 | 2 | 5.38 | 4.80 | 5.96 | | | |
| LYO | 35 | 70 | 4.36 | 4.16 | 4.56 | 1.03 | 0.42 | 1.63 |
| LYO | 70 | 19 | 3.87 | 3.69 | 4.06 | 1.51 | 0.91 | 2.12 |

CI: confidence interval

TABLE 8

Intercept and slope (viral titer titer loss per day) for OTF batches P#165 to P#198

| | Intercept | | | | Slope (viral titer titer loss per day) | | | |
|---|---|---|---|---|---|---|---|---|
| OTF batch | Estimate | StdErr | Lower 95% CI | Upper 95% CI | Estimate | StdErr | Lower 95% CI | Upper 95% CI |
| P#165 | 5.252 | 0.0585 | 5.129 | 5.376 | −0.008 | 0.0013 | −0.010 | −0.005 |
| P#166 | 5.152 | 0.0461 | 5.055 | 5.249 | −0.005 | 0.0010 | −0.007 | −0.003 |
| P#167 | 5.299 | 0.0736 | 5.144 | 5.455 | −0.014 | 0.0016 | −0.018 | −0.011 |
| P#168 | 5.501 | 0.0475 | 5.401 | 5.601 | −0.010 | 0.0011 | −0.012 | −0.007 |
| P#169 | 5.397 | 0.0666 | 5.256 | 5.537 | −0.011 | 0.0015 | −0.014 | −0.008 |
| P#170 | 5.331 | 0.0464 | 5.233 | 5.429 | −0.004 | 0.0010 | −0.006 | −0.002 |
| P#171 | 5.335 | 0.0872 | 5.151 | 5.519 | −0.013 | 0.0019 | −0.017 | −0.009 |
| P#172 | 4.706 | 0.1886 | 4.308 | 5.104 | −0.018 | 0.0042 | −0.027 | −0.010 |
| P#173 | 4.753 | 0.1891 | 4.354 | 5.152 | −0.020 | 0.0042 | −0.029 | −0.011 |
| P#174 | 4.999 | 0.1702 | 4.640 | 5.358 | −0.022 | 0.0038 | −0.030 | −0.014 |
| P#175 | 5.158 | 0.1446 | 4.853 | 5.463 | −0.013 | 0.0032 | −0.020 | −0.006 |
| P#176 | 5.316 | 0.1491 | 4.998 | 5.634 | −0.020 | 0.0034 | −0.027 | −0.012 |
| P#177 | 5.455 | 0.0514 | 5.346 | 5.563 | −0.010 | 0.0011 | −0.013 | −0.008 |
| P#178 | 5.250 | 0.0670 | 5.109 | 5.391 | −0.014 | 0.0015 | −0.017 | −0.011 |
| P#179 | 5.386 | 0.1510 | 5.067 | 5.704 | −0.025 | 0.0034 | −0.032 | −0.018 |
| P#180 | 5.540 | 0.1159 | 5.296 | 5.785 | −0.019 | 0.0026 | −0.024 | −0.013 |
| P#181 | 5.110 | 0.1359 | 4.823 | 5.396 | −0.009 | 0.0030 | −0.016 | −0.003 |
| P#182 | 5.534 | 0.1016 | 5.320 | 5.749 | −0.026 | 0.0023 | −0.031 | −0.021 |
| P#183 | 5.113 | 0.1584 | 4.778 | 5.447 | −0.007 | 0.0035 | −0.014 | 0.001 |
| P#184 | 5.202 | 0.2077 | 4.764 | 5.640 | −0.007 | 0.0046 | −0.017 | 0.002 |
| P#185 | 5.388 | 0.1136 | 5.148 | 5.627 | −0.018 | 0.0025 | −0.023 | −0.013 |
| P#186 | 5.186 | 0.1373 | 4.897 | 5.476 | −0.014 | 0.0031 | −0.020 | −0.007 |
| P#187 | 5.235 | 0.0712 | 5.085 | 5.385 | −0.002 | 0.0016 | −0.006 | 0.001 |
| P#188 | 5.558 | 0.1494 | 5.243 | 5.873 | −0.015 | 0.0033 | −0.022 | −0.008 |
| P#189 | 5.242 | 0.0437 | 5.149 | 5.334 | −0.006 | 0.0010 | −0.009 | −0.004 |
| P#190 | 5.212 | 0.0967 | 5.008 | 5.417 | −0.024 | 0.0022 | −0.029 | −0.020 |
| P#191 | 5.255 | 0.1255 | 4.990 | 5.520 | −0.024 | 0.0028 | −0.029 | −0.018 |
| P#192 | 4.961 | 0.1255 | 4.696 | 5.225 | −0.022 | 0.0028 | −0.028 | −0.016 |
| P#193 | 5.355 | 0.0431 | 5.264 | 5.446 | −0.008 | 0.0010 | −0.010 | −0.006 |
| P#194 (benchmark) | 5.302 | 0.0826 | 5.128 | 5.476 | −0.012 | 0.0018 | −0.016 | −0.008 |
| P#195 | 5.332 | 0.0416 | 5.242 | 5.422 | −0.002 | 0.0010 | −0.004 | 0.000 |
| P#196 | 5.428 | 0.0421 | 5.337 | 5.519 | −0.007 | 0.0010 | −0.009 | −0.004 |
| P#197 | 5.561 | 0.1003 | 5.345 | 5.778 | −0.006 | 0.0021 | −0.011 | −0.001 |
| P#198 | 5.482 | 0.0620 | 5.349 | 5.615 | −0.009 | 0.0014 | −0.012 | −0.006 |
| Rota Lyo | 5.025 | 0.1675 | 4.686 | 5.364 | −0.017 | 0.0031 | −0.023 | −0.011 |

This data showed that an optimal slope of (−0.002) was observed for the OTF formulation P #187 which also had a good flexibility.

Figure 17:
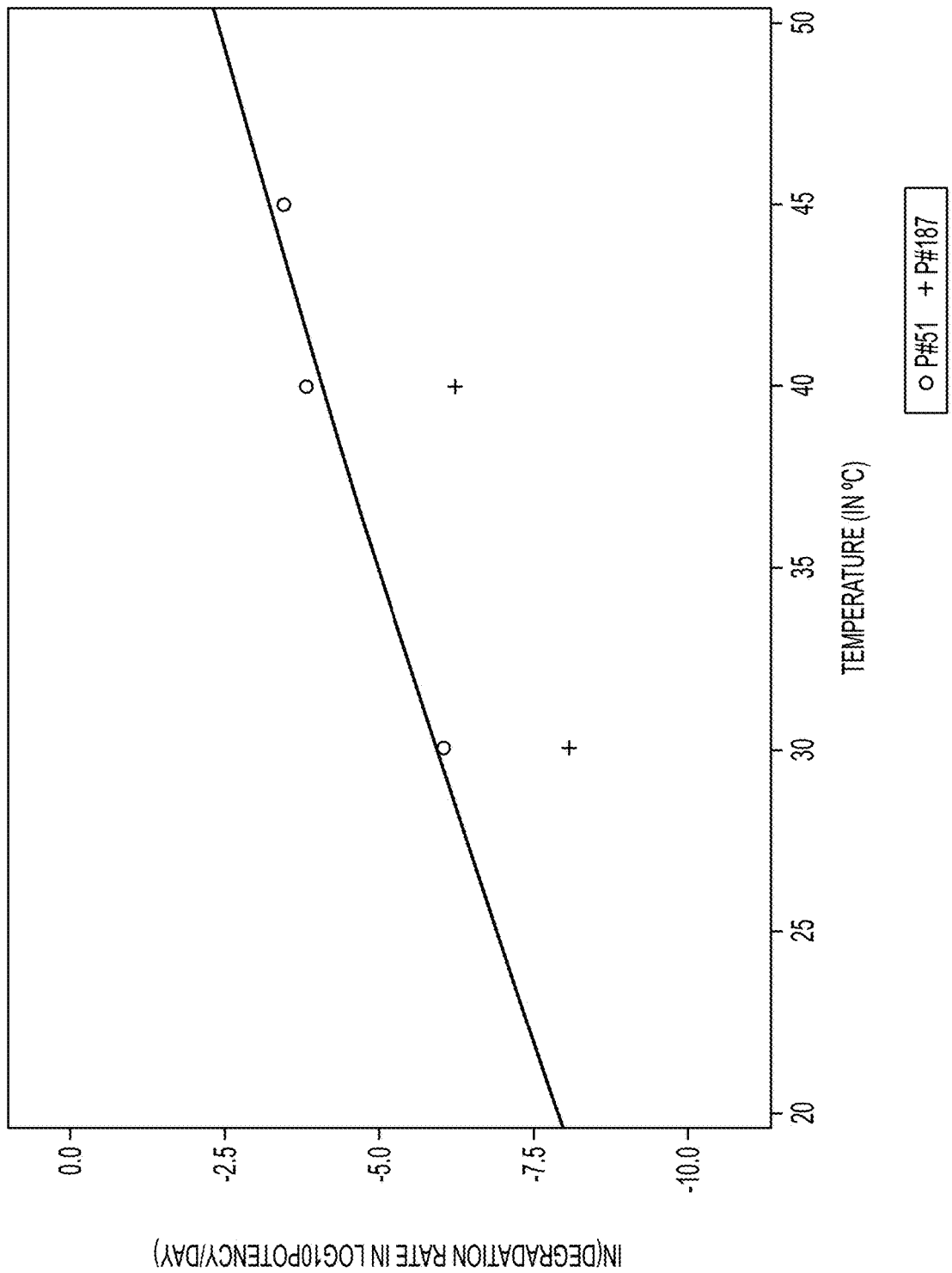
FIG. 17—Prediction of degradation rate at 30° C. based on Arrhenius model for OTF formulation P #187.

The log of the slope from OTF formulation P #187 (−0.002) was plotted against the temperature at 40° C. Assuming the relationship between the decay rate and the temperature is the same as for the base OTF formulation P #51, the model described in Example 3 predicted a slope of −0.000322 log 10 (ffu/ml)/day (ln slope of −8.0409) at 30° C., i.e. a mean loss of 0.235 in $\log_{10}$ ffu/ml after 2 years at 30° C. (see FIG. 17). A similar computation was done for a storage at 20° C. and 25° C., the results of which are presented in Table 9.

TABLE 9

Potency loss prediction after 2 years by Arrhenius model

| Temperature | Predicted potency loss ($\log_{10}$ ffu/ml) |
|---|---|
| 20° C. | 0.03 |
| 25° C. | 0.09 |
| 30° C. | 0.23 |

What is claimed is:

1. A quick-dissolving thin film comprising a virus and an excipient mix, wherein said excipient mix comprises
one or more water-soluble polymer(s),
trehalose,
a metal ion,
a carboxylate, and
a buffering agent,
wherein said quick-dissolving thin film is thermostable, and
wherein said quick-dissolving thin film does not comprise any animal derived product or gelatin.

2. The quick-dissolving thin film of claim 1, wherein said virus is selected from a live virus, a live attenuated virus, an inactivated virus or a reassortant virus.

3. The quick-dissolving thin film of claim 2, wherein the virus is a rotavirus, wherein the rotavirus is a live attenuated rotavirus.

4. The quick-dissolving thin film of claim 1, wherein said metal ion is selected from $Zn^{2+}$ and $Mn^{2+}$.

5. The quick-dissolving thin film of claim 1, wherein the carboxylate is citric acid.

6. The quick-dissolving thin film of claim 1, wherein said buffering agent is selected from phosphate buffer and histidine base.

7. The quick-dissolving thin film of claim 1, wherein said excipient mix further comprises one or more amino acids, selected from at least one of glycine and arginine.

8. The quick-dissolving thin film of claim 1, wherein the virus is present in the quick-dissolving thin film of the invention at a titer ranging from about $1 \times 10^5$ to about $1 \times 10^{11}$ ffu per dose, and wherein the excipient mix comprises or consists of between 30% and 90% by weight of the water-soluble polymer(s),
between 10% and 60% by weight of trehalose,
between 0.01% and 1% by weight of the metal ion or salt,
between 0.5% and 5% by weight of the carboxylate,
between 0.5% and 5% by weight of the buffering agent, and
between 0% and 20% by weight of one or more amino acids.

9. The quick-dissolving thin film of claim 1, wherein in the excipient mix,
the water-soluble polymer is PVA,
the sugar is trehalose,
the metal ion is in the form of $ZnCl_2$,
the carboxylate is citric acid,
the buffering agent is selected from $K_2HPO_4$ and histidine base, and
the one or more amino acids, if present, are selected from arginine and/or glycine.

10. The quick-dissolving thin film of claim 9, wherein the virus is a rotavirus.

11. The quick-dissolving thin film of claim 10, wherein the rotavirus is present in the quick-dissolving thin film of the invention at a titer ranging from about $1 \times 10^5$ to about $1 \times 10^8$ ffu per dose.

12. The quick-dissolving thin film of claim 9, wherein the excipient mix comprises or consists of
a. between 30% and 90% by weight of PVA,
b. between 10% and 60% by weight of trehalose,
c. between 0.01% and 1%, by weight of $ZnCl_2$,
d. between 0.5% and 5% by weight of citric acid,
e. between 0.5% and 5% by weight of $K_2HPO_4$ or histidine base,
f. between 0% and 10% by weight of arginine and,
g. between 0% and 5%, by weight of glycine.

13. The quick-dissolving thin film of claim 1, wherein said quick-dissolving thin film further comprises an antacid.

14. The quick-dissolving thin film of claim 13, wherein the excipient mix: antacid ratio (w/w) is from about 1:3 to about 2:1, from about 1:2 to 1.5:1, or from about 1:1.5 to 1:1.

15. The quick-dissolving thin film of claim 1, wherein said quick-dissolving thin film has a surface pH between 5 and 9.

16. The quick-dissolving thin film of claim 1, wherein said quick-dissolving thin film has a thickness of less than 500 μm.

17. The quick-dissolving thin film of claim 1, wherein said quick-dissolving thin film has a moisture content lower than about 10% by weight.

18. A method for the treatment of an infectious disease in a subject comprising administering the quick-dissolving thin film of claim 1 to a subject.

19. A kit comprising the quick-dissolving thin film of claim 1 in a sterile packaging and instructions for use of the kit.

20. A method for preparing a thermostable quick-dissolving thin film comprising:
a) preparing an aqueous solution comprising or consisting of
a virus,
one or more water-soluble polymer(s),
trehalose,
a metal ion,
a carboxylate, and
one or more buffering agents,
wherein said aqueous solution does not comprise any animal derived product or gelatin,
b) adjusting the pH of the aqueous solution to a value comprised between 5 and 9,
c) applying the aqueous solution on a drying surface,
d) drying the aqueous solution to obtain a thin film, and
e) removing the dried thin film from the drying surface, thereby obtaining said thermostable quick-dissolving thin film.

* * * * *